(12) United States Patent
Xu et al.

(10) Patent No.: US 10,418,693 B2
(45) Date of Patent: Sep. 17, 2019

(54) BAND LATCH MECHANISM AND HOUSING WITH INTEGRATED ANTENNA

(71) Applicant: Fitbit, Inc., San Francisco, CA (US)

(72) Inventors: Nan Xu, San Diego, CA (US); Christos Kinezos Ioannou, San Diego, CA (US); Kevin Li, San Diego, CA (US); Chadwick John Harber, San Francisco, CA (US); Eric John Fairbanks, Lafayette, CA (US); Jonah Avram Becker, San Francisco, CA (US)

(73) Assignee: Fitbit, Inc., San Francisco, CA (US)

(*) Notice: Subject to any disclaimer, the term of this patent is extended or adjusted under 35 U.S.C. 154(b) by 0 days.

(21) Appl. No.: 15/820,928

(22) Filed: Nov. 22, 2017

(65) Prior Publication Data

US 2018/0294554 A1 Oct. 11, 2018

Related U.S. Application Data

(63) Continuation-in-part of application No. 15/627,915, filed on Jun. 20, 2017.

(60) Provisional application No. 62/547,621, filed on Aug. 18, 2017, provisional application No. 62/483,951, filed on Apr. 11, 2017.

(51) Int. Cl.
| | |
|---|---|
| *H01Q 1/27* | (2006.01) |
| *H01Q 1/24* | (2006.01) |
| *A61B 5/00* | (2006.01) |
| *A44C 5/14* | (2006.01) |
| *A44C 5/00* | (2006.01) |
| *G04G 21/04* | (2013.01) |
| *G04R 60/06* | (2013.01) |
| *H01Q 5/30* | (2015.01) |
| *H01Q 21/28* | (2006.01) |
| *A61B 5/11* | (2006.01) |

(52) U.S. Cl.
CPC .......... *H01Q 1/273* (2013.01); *A44C 5/0053* (2013.01); *A44C 5/14* (2013.01); *A61B 5/681* (2013.01); *A61B 5/6831* (2013.01); *G04G 21/04* (2013.01); *G04R 60/06* (2013.01); *H01Q 1/241* (2013.01); *A61B 5/002* (2013.01); *A61B 5/0059* (2013.01); *A61B 5/1112* (2013.01); *A61B 5/7445* (2013.01); *H01Q 5/30* (2015.01); *H01Q 21/28* (2013.01)

(58) Field of Classification Search
CPC .......... H01Q 1/273; H01Q 1/241; H01Q 5/30; H01Q 21/28; A61B 5/0059; A61B 5/681
USPC ....................................................... 341/702
See application file for complete search history.

(56) References Cited

U.S. PATENT DOCUMENTS

| | | | |
|---|---|---|---|
| 2006/0044201 A1* | 3/2006 | Arnold ................. | H01Q 9/0442 343/772 |
| 2015/0255871 A1* | 9/2015 | Baringer .............. | A61B 5/0002 343/702 |

(Continued)

*Primary Examiner* — Peguy Jean Pierre
(74) *Attorney, Agent, or Firm* — Weaver Austin Villeneuve & Sampson LLP

(57) ABSTRACT

A band latch mechanism that is configured to connect a wristband to a fitness tracker is provided. The band latch mechanism may be configured to be inserted into a cavity of a housing of the fitness tracker and configured so that any metallic body of the band latch mechanism does not contact metallic surfaces of the cavity in order to prevent an electrical ground from being positioned within a keep-out zone of an antenna of the fitness tracker. A housing with integrated antenna structures is also disclosed.

23 Claims, 21 Drawing Sheets

(56) References Cited

U.S. PATENT DOCUMENTS

| | | | |
|---|---|---|---|
| 2015/0364813 A1* | 12/2015 | Darnell | H01Q 1/243 |
| | | | 343/702 |
| 2016/0056533 A1* | 2/2016 | Nissinen | H01Q 9/0421 |
| | | | 343/702 |
| 2016/0064820 A1* | 3/2016 | Kim | H01Q 1/243 |
| | | | 343/767 |
| 2017/0187096 A1* | 6/2017 | Hwang | H01Q 1/273 |

\* cited by examiner

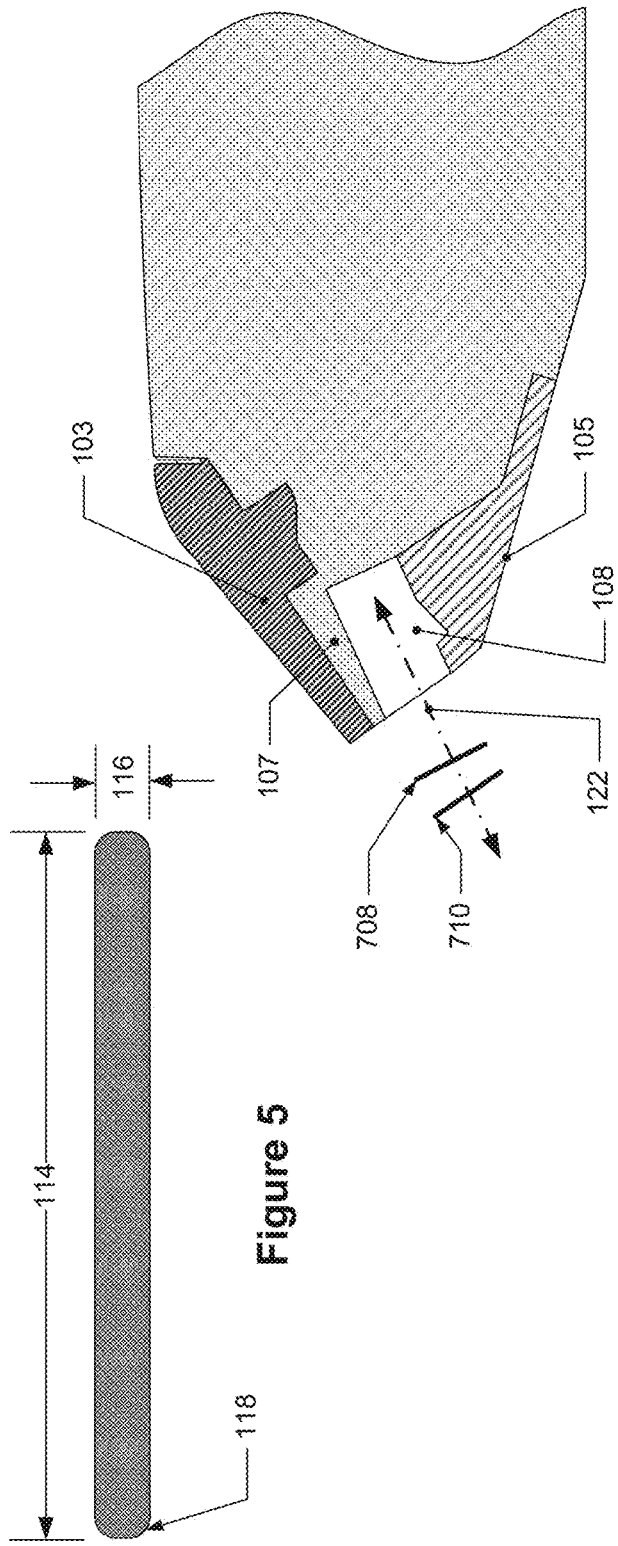
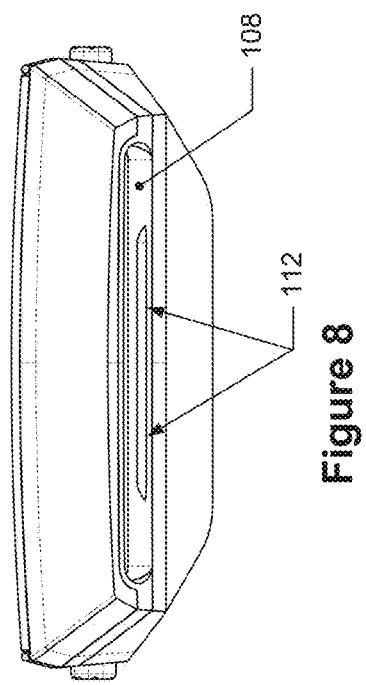
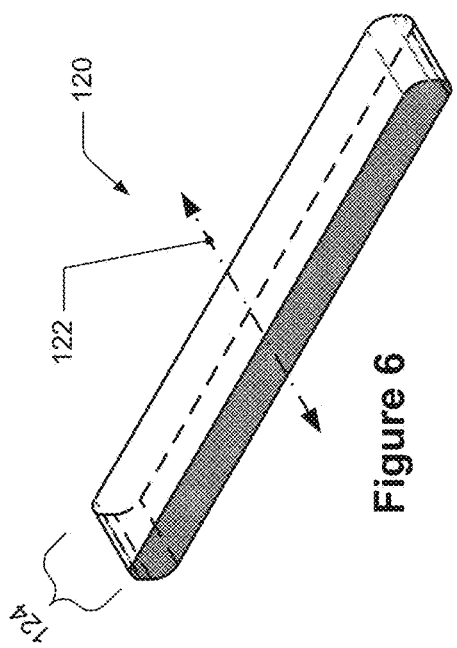

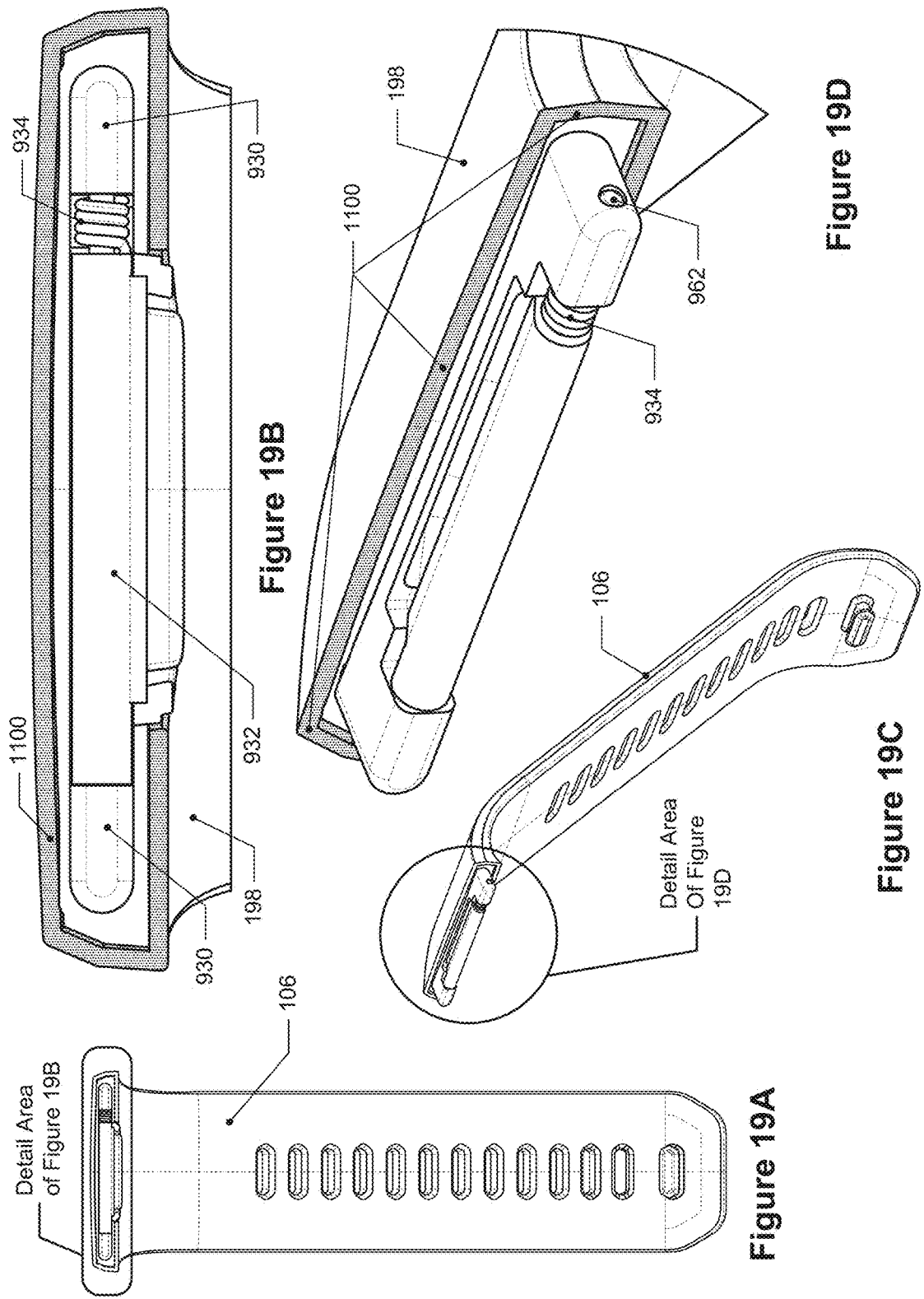

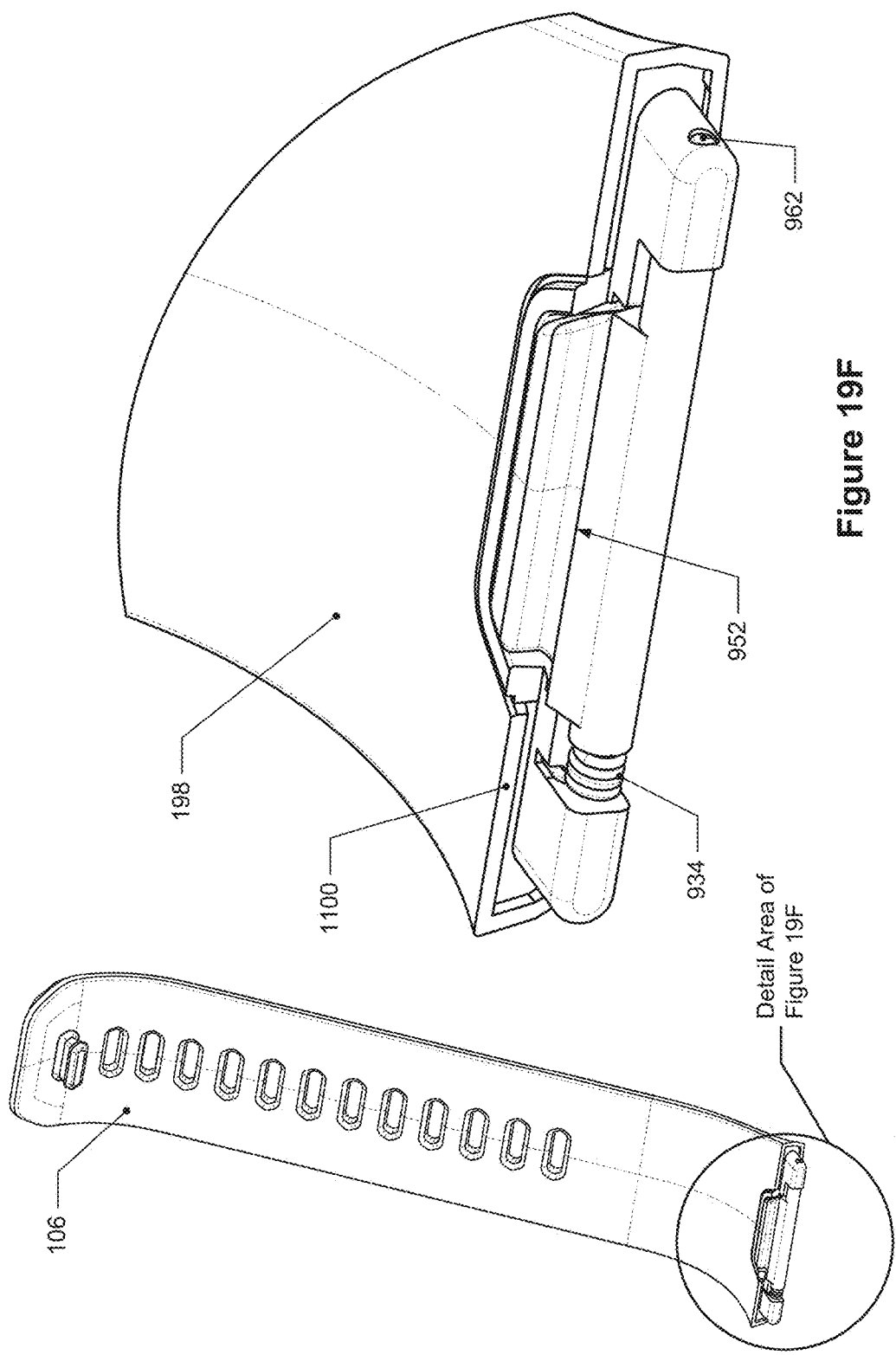

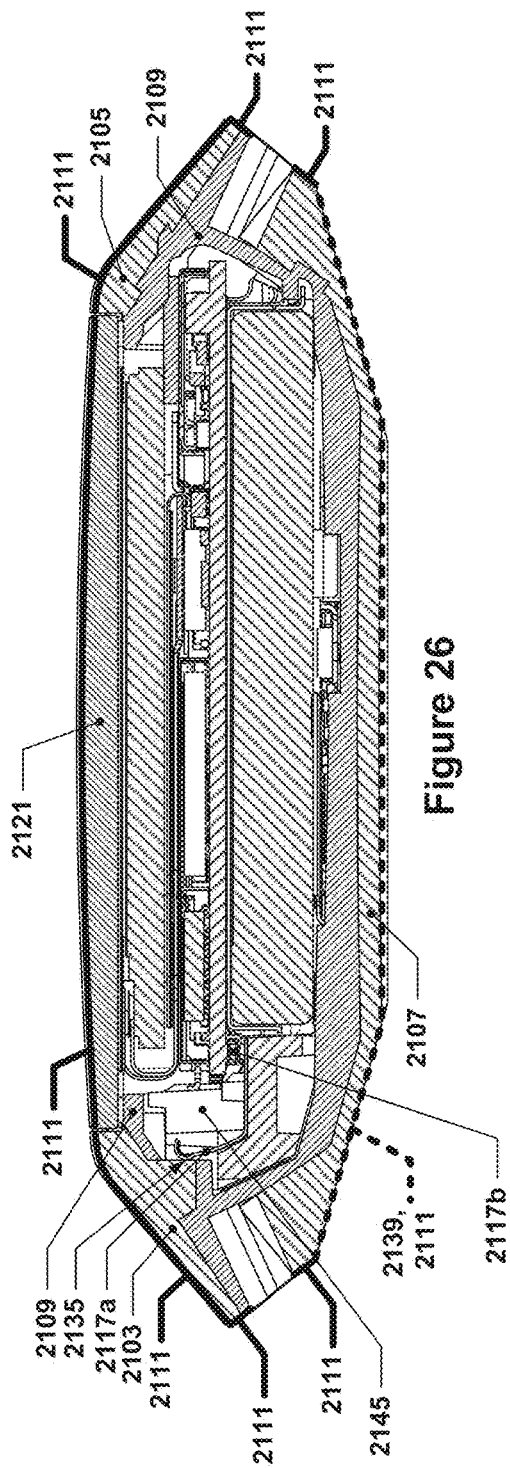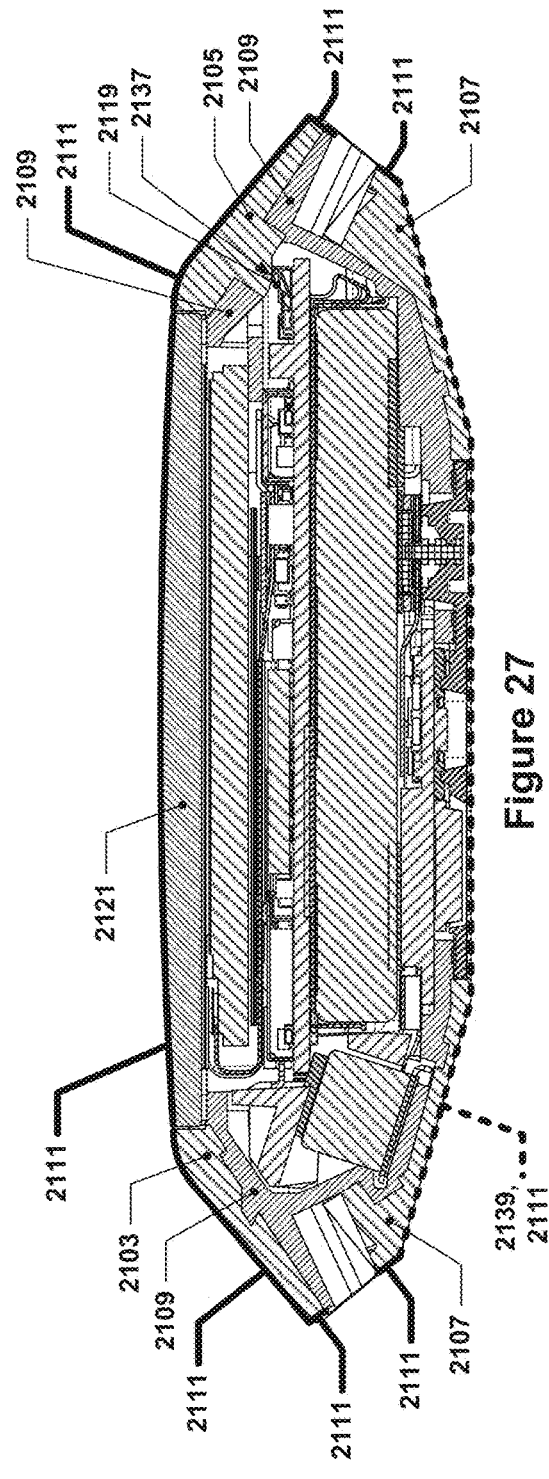

BAND LATCH MECHANISM AND HOUSING WITH INTEGRATED ANTENNA

CROSS-REFERENCE TO RELATED APPLICATION

This application is a continuation-in-part under 35 U.S.C. § 120 of U.S. patent application Ser. No. 15/627,915, filed Jun. 20, 2017, which claims benefit of priority under 35 U.S.C. § 119(e) to U.S. Provisional Patent Application No. 62/483,951, filed Apr. 11, 2017, and titled "WATCH BAND LATCH AND BUCKLE," both of which are hereby incorporated by reference herein in their entireties, and also claims benefit of priority under 35 U.S.C. § 119(e) to U.S. Provisional Patent Application No. 62/547,621, filed Aug. 18, 2017, and titled "BAND LATCH MECHANISM AND HOUSING WITH INTEGRATED ANTENNA," which is also hereby incorporated by reference herein in its entirety.

BACKGROUND

Personal fitness and health monitoring devices, which may be referred to as biometric monitoring devices or fitness trackers herein, may be worn by a user on various locations on the user's body, such as around the user's wrist or ankle. Wristband straps may be attached to a housing of the biometric monitoring device, wrapped around the user's wrist, and joined together to form a loop that may appear to be a bracelet or wristband. Some biometric monitoring devices may include wireless receivers and/or transmitters to allow them to communicate with external devices, such as smartphones, or to receive signals such as GPS (Global Positioning System) signals or other GNSS (Global Navigation Satellite System) signals.

SUMMARY

Details of one or more implementations of the subject matter described in this specification are set forth in the accompanying drawings and the description below. Other features, aspects, and advantages will become apparent from the description, the drawings, and the claims.

In one embodiment, an apparatus may be provided. The apparatus may include a body portion that is configured to be connected to a band and includes a recess with a first cross-sectional area when viewed along a direction perpendicular to a top surface of the body portion, and an insertion portion that extends away from the body portion and is contained within a prismatic reference volume that extends away from the body portion in a first direction. The prismatic reference volume may have a second cross-sectional area in a plane perpendicular to the first direction, the second cross-sectional area may have a rounded-corner rectangular shape of substantially 26.8 millimeters by substantially 2.16 millimeters and corners radiused substantially 0.80 millimeters, and the insertion portion may have at least a third cross-sectional area in a plane perpendicular to the first direction that is circumscribed by the rounded-corner rectangular shape. The apparatus may also include a latching portion that has a latching edge that is configured to be displaceable between a first position and a second position. In the first position, the latching edge may be outside the prismatic volume, and in the second position, the latching edge may be within the prismatic volume. The apparatus may further include a force biasing portion that is configured to cause the latching edge to be in the first position and the recess may be configured to permit the movement of the latching portion between the first position and the second position.

In some embodiments, the insertion portion and the latching portion may both be comprised of a non-metallic material.

In some embodiments, the exterior surface of the insertion portion and the exterior surface of the latching portion may both be comprised of a non-metallic material.

In some embodiments, the surfaces of the insertion portion and the latching portion that contact a housing of a fitness monitoring device when the insertion portion and the latching portion are inserted into a cavity of the housing may be comprised of a non-metallic material.

In some embodiments, in the first position, when the insertion portion and the latching portion are inserted into a cavity of a housing of a fitness monitoring device, the latching edge may be located within a notch of the cavity.

In some embodiments, the latching portion may be rotatably connected to the insertion portion such that the latching portion is rotatable about a rotation axis.

In some such embodiments, the apparatus may further include a pin, the insertion portion may further include a first protrusion and a second protrusion that are offset from each other in a second direction that is perpendicular to the first direction, the rotation axis may extend between the first protrusion and the second protrusion, a first end of the pin may be positioned in the first protrusion, a second end of the pin may be positioned in the second protrusion, the pin may extend between the first protrusion and the second protrusion, the latching portion may further include a latching body having a hole that extends through the latching body in a direction parallel to the latching edge, and the pin may extend through the hole of the latching body to rotatably connect the latching portion to the first protrusion and the second protrusion, such that the latching portion is rotatable about the pin.

In some further such embodiments, the insertion portion and the latching portion may be both comprised of a non-metallic material, and the force biasing portion and the pin may both be comprised of a metallic material.

In some additional embodiments, the force biasing portion may be within the prismatic reference volume, and the pin may be within the prismatic reference volume.

In some other further such embodiments, the force biasing portion may be a torsion spring, a first end of the torsion spring may be connected to the latching portion, a second end of the torsion spring may contact one or more of the body portion and the insertion portion, a first section of the torsion spring may be coiled around the pin, when the latching edge is in the first position, the torsion spring may be deflected by a first amount, and when the latching portion is in the second position, the torsion spring may be deflected by a second amount that is greater than the first amount.

In some additional embodiments, the torsion spring may have four active coils, a mean coil diameter of substantially 1.35 millimeters, a wire diameter of substantially 0.35 millimeters, and a deflection angle of at least 20 degrees.

In some other such embodiments, the rotational distance between the first position and the second position may be about twenty degrees.

In some embodiments, a first width of the insertion portion may be substantially 26.6 millimeters, a first thickness of the insertion portion may be substantially 2 millimeters, and a first length of the insertion portion may be substantially 3.1 millimeters.

In some embodiments, the latching portion may further include a latching lever that is connected to the latching edge, and the latching lever may have a fourth cross-sectional area in a plane perpendicular to the first direction that is less than the first cross-sectional area of the recess.

In some embodiments, the latching portion may further include a first surface and a second surface that intersect to form the latching edge.

In some such embodiments, the internal angle between the first surface and the second surface may be about 95 degrees or less.

In some embodiments, the body portion may be connected to the band, the band may include a band body portion and a rib, the rib may be comprised of a compliant material, may extend from the band body portion, and may extend around a section of the body portion, the insertion portion, and the latching portion.

In some such embodiments, the rib may be compressible by substantially 0.03 millimeters.

In some embodiments, the latching portion may be contiguous with the insertion portion. In some other embodiments, the latching portion may not be contiguous with the insertion portion.

In some embodiments, the body portion may be contiguous with the insertion portion. In some other embodiments, the body portion may not be contiguous with the insertion portion.

In some implementations, an apparatus may be provided that includes a first radio-frequency (RF) receiver having a first RF feed and a housing configured to be part of a wearable electronic device, such as a wearable fitness tracker or watch. In such embodiments, the first RF receiver and the first RF feed may be located within the housing and the housing may have a plurality of exterior surfaces and may also include a base portion, a first RF radiator portion, and an electrically non-conductive intermediate structure that is interposed between, and connected with, the base portion and the first RF radiator portion. The base portion may include a back surface that faces a wearer's skin that contacts the wearable electronic device when the wearable electronic device is worn by the wearer, and the base portion and the first RF radiator portion may be made of metal. The first RF radiator portion may include one or more of the exterior surfaces of the housing, the first RF radiator portion may be positioned within the housing such that the exterior surfaces of the housing included in the first RF radiator portion generally face away from the back surface, and the first RF radiator portion may be in electrically conductive contact with the first RF feed within the housing.

In some implementations of the apparatus, the electrically non-conductive intermediate structure may maintain a separation distance of between 0.8 and 1.5 mm between the first RF radiator portion and the base portion.

In some implementations of the apparatus, the first RF radiator portion may be electrically isolated from the base portion by the electrically non-conductive intermediate structure.

In some implementations of the apparatus, the base portion and the first RF radiator portion may be made of a non-ferrous metal.

In some implementations of the apparatus, the base portion, the first RF radiator portion, and the electrically non-conductive intermediate structure may be a nano-molded structure, with the first RF radiator portion and the base portion each having a plurality of microscopic fissures or pores arising from the nano-molding manufacturing process and the electrically non-conductive intermediate structure having portions extending into the microscopic fissures or pores.

In some implementations of the apparatus, the base portion and the first RF radiator portion may be bonded to the electrically non-conductive intermediate structure with an adhesive layer.

In some implementations of the apparatus, the apparatus may further include a second RF receiver having a second RF feed. In such implementations, the second RF receiver and the second RF feed may be located within the housing, the housing further may include a second RF radiator portion, the electrically non-conductive intermediate structure may be further interposed between, and connected with, the base portion and the second RF radiator portion, and the second RF radiator portion may be made of metal. Furthermore, in such implementations, the second RF radiator portion may include one or more further exterior surfaces of the housing and may be positioned within the housing such that the further exterior surfaces of the housing included in the second RF radiator portion generally face away from the back surface. The second RF radiator portion may also be in electrically conductive contact with the second RF feed within the housing and be electrically isolated from the base portion and the first RF radiator portion by the electrically non-conductive intermediate structure. The electrically non-conductive intermediate structure may, in such implementations, maintain a separation distance of between 0.8 and 1.5 mm between the second RF radiator portion and the base portion.

In some implementations of the apparatus, the first RF receiver may be configured to operate in one or more first frequency bands that are in the 600 MHz to 2200 MHz range, and the second RF receiver may be configured to operate in one or more second frequency bands that are in the 1.5 GHz to 2.7 GHz range.

In some implementations of the apparatus, the apparatus may also include a display unit that is mounted in the housing such that a display surface of the display unit generally faces away from the back surface and such that the first RF radiator portion is positioned next to the display unit.

In some implementations of the apparatus, the wearable electronic device may be a wrist-wearable device and the apparatus may further include at least one wrist strap that is connected to the housing. The housing may have a transverse axis that is substantially aligned with the wearer's forearm when the apparatus is worn on the wearer's forearm, and the first RF radiator portion may have a first dimension along the transverse axis that is between 3 and 7 times longer than the longest dimension of the first RF radiator portion along an axis perpendicular to the transverse axis.

In some implementations of the apparatus, the housing may have a centerline that is perpendicular to the transverse axis and nominally parallel to the back surface, and the first RF feed may make electrically conductive contact with the first RF radiator portion in a location located on a side of the centerline closer to the wearer's left hand when the apparatus is worn by the wearer on the wearer's left forearm.

In some implementations of the apparatus, the location where the first RF feed makes electrically conductive contact with the first RF radiator portion may be in a region of the first RF radiator portion that is within an outermost 25% of the first RF radiator portion that is closest to the wearer's left hand when the apparatus is worn by the wearer on the wearer's left forearm.

In some implementations of the apparatus, the apparatus may further include a second RF receiver that has a second RF feed. In such implementations, the second RF receiver and the second RF feed may be located within the housing, which may further include a second RF radiator portion. The electrically non-conductive intermediate structure may be further interposed between, and connected with, the base portion and the second RF radiator portion, and the second RF radiator portion may be made of metal. The second RF radiator portion may include one or more further exterior surfaces of the housing and may be positioned within the housing such that the further exterior surfaces of the housing included in the second RF radiator portion generally face away from the back surface. The second RF radiator portion may also be in electrically conductive contact with the second RF feed within the housing and may be electrically isolated from the base portion and the first RF radiator portion by the electrically non-conductive intermediate structure. In such implementations, the electrically non-conductive intermediate structure may maintain a separation distance of between 0.8 and 1.5 mm between the second RF radiator portion and the base portion.

In some implementations of the apparatus, the second RF radiator portion may have a second dimension along the transverse axis that is between 3 and 7 times longer than the longest dimension of the second RF radiator portion along the axis perpendicular to the transverse axis.

In some implementations of the apparatus, the second RF feed may make electrically conductive contact with the second RF radiator portion in a location that is within a first distance of the centerline that is within 10% of the second dimension.

In some implementations of the apparatus, the location where a second RF feed makes electrically conductive contact with the second RF radiator portion may be on the centerline.

In some implementations of the apparatus, the first RF receiver may be configured to operate in one or more first frequency bands that are in the 600 MHz to 2200 MHz range, and a second RF receiver may be configured to operate in one or more second frequency bands that are in the 1.5 GHz to 2.7 GHz range.

In some implementations of the apparatus, the base portion, the first RF radiator portion, the second RF radiator portion, and the electrically non-conductive intermediate structure may be a nano-molded structure, with the first RF radiator portion, the second RF radiator portion, and the base portion each having a plurality of microscopic fissures or pores and the electrically non-conductive intermediate structure having portions extending into the microscopic fissures or pores.

In some implementations of the apparatus, the apparatus may further include a display unit that is mounted in the housing such that a display surface of the display unit generally faces away from the wearer's skin that is placed into contact with the back surface when the wearable electronic device is worn by the wearer, and the first RF radiator portion and the second RF radiator portions may be positioned next to, and adjacent to opposing sides of, the display unit.

In some implementations of the apparatus, the housing may be configured to be connected with a first band portion such that the first band portion is adjacent to the first RF radiator portion and with a second band portion such that the second band portion is adjacent to the second RF radiator portion, the edges of the first RF radiator portion and the second RF radiator portion that are adjacent to the display unit may have a length that is within ±5% of the length of the edges of the display unit that are adjacent to the first RF radiator portion and the second RF radiator portion, respectively, and the edges of the first RF radiator portion and the second RF radiator portion that are furthest from the display unit may have a length that is within ±5% of the length of the edges of the first band portion and the second band portion that are adjacent to the first RF radiator portion and the second RF radiator portion, respectively, when the first band portion and the second band portion are connected with the housing.

In some implementations, a method may be provided that includes providing a metal base portion and a first RF radiator portion also made of metal, positioning the metal base portion and the first RF radiator portion in a spaced-apart configuration in an injection molding die such that the closest points of the first RF radiator portion and the base portion are within 0.8 mm to 1.5 mm apart, and injecting molten plastic into the injection molding die.

In some implementations, an apparatus may be provided that includes a first radio-frequency (RF) receiver means with a first RF feed means and a housing configured to be part of a wearable electronic device. In such an implementation, the first RF receiver and the first RF feed may be located within the housing, the housing may have a plurality of exterior surfaces and may include a base portion, a first RF radiator means, and an electrically non-conductive intermediate structure that is interposed between, and connected with, the base portion and the first RF radiator means, and the base portion may include a back surface that faces a wearer's skin that contacts the wearable electronic device when the wearable electronic device is worn by the wearer. In such implementations, the base portion and the first RF radiator means may be made of metal, the first RF radiator means may include one or more of the exterior surfaces of the housing, the first RF radiator means may be positioned within the housing such that the exterior surfaces of the housing included in the first RF radiator means generally face away from the back surface, and the first RF radiator means may be in electrically conductive contact with the first RF feed within the housing.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIG. 5 depicts the cross-sectional area of a representational volume.

FIG. 6 depicts an isometric view of the representational volume that is bounded by a cavity of the housing.

FIG. 7 depicts a partial cross-sectional side view of the housing.

FIG. 8 depicts a different front view of the housing of the fitness tracker of FIG. 1.

FIG. 19A depicts a front view of the band latch mechanism connected to a wristband of FIG. 2.

FIG. 19B depicts a detail view of FIG. 19B.

FIG. 19C depicts an off-angle view of the band latch mechanism of FIG. 19A.

FIG. 19D depicts a detail view of FIG. 19C.

FIG. 19E depicts another off-angle view of the band latch mechanism of FIG. 19A.

FIG. 19F depicts a detail view of FIG. 19E.

FIG. 26 depicts a further cross-sectional view of the example biometric monitoring device of FIG. 22 taken through a sectioning plane offset from a mid-plane of the housing.

FIG. 27 depicts a cross-sectional view of the example biometric monitoring device of FIG. 22 taken through the mid-plane of the housing.

FIGS. 1 through 27 are drawn to-scale within each Figure, although not necessarily to the same scale from Figure to Figure.

DETAILED DESCRIPTION

Importantly, the concepts discussed herein are not limited to any single aspect or implementation discussed herein, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

Biometric monitoring devices, also referred to as fitness trackers, are generally worn on a user's body, such as around the user's wrist or ankle. Many fitness trackers include a housing that houses electronics for monitoring various health-related parameters, including, but not limited to, steps taken, calories burned, etc., as well as for transmitting data relating to such monitored parameters. For those fitness trackers worn around a user's wrist, they may include a wristband that attaches to the housing and is used to secure the fitness tracker around the user's wrist. The wristband may include two wristband straps that are flexible to allow the ends of the wristband straps to be joined together using a buckle component (or other fastening mechanism) to form a loop. When the ends of the wristband straps are joined together, the fitness trackers may appear to be a bracelet or wristband. The housings of such fitness trackers may have identical (or nearly identical) interfaces on each end that may receive features from a wristband strap which enable the wristband strap to be connected to the housing and also be removable from the housing so that replacement wristbands or wristbands of different sizes or styles may be exchanged and connected to the housing.

Figure 2:
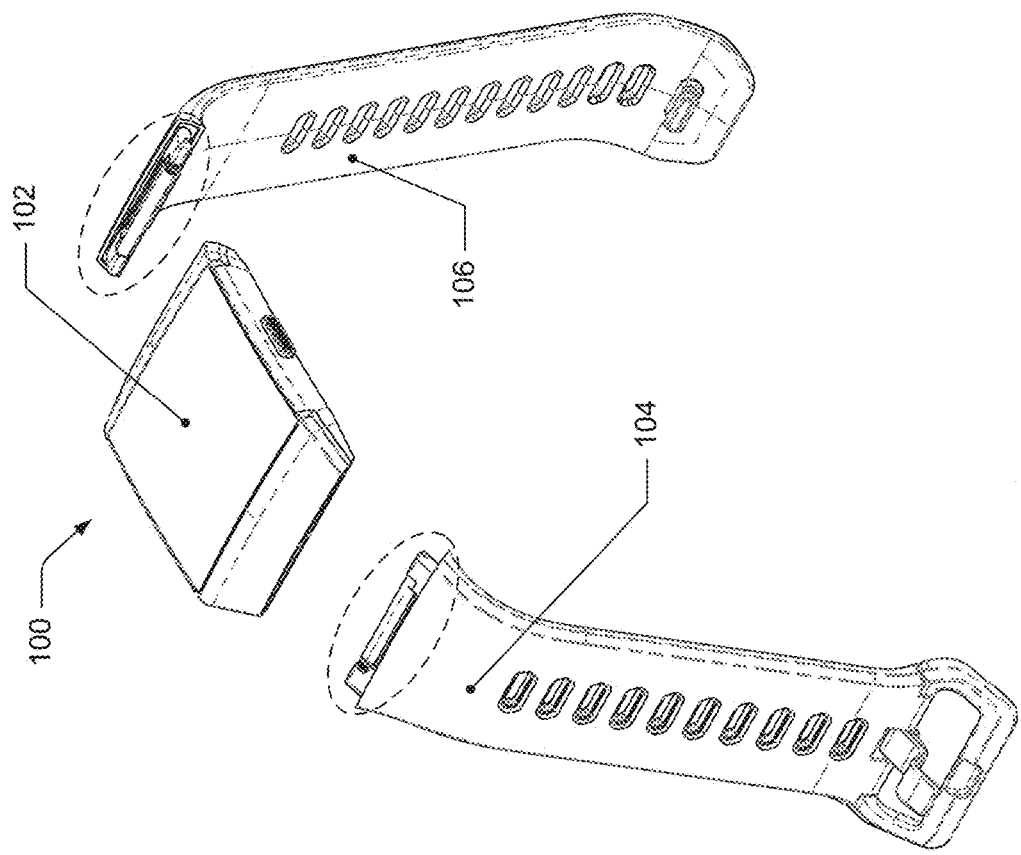
FIG. 2 depicts an exploded isometric view of the fitness tracker of FIG. 1.
Figure 1:
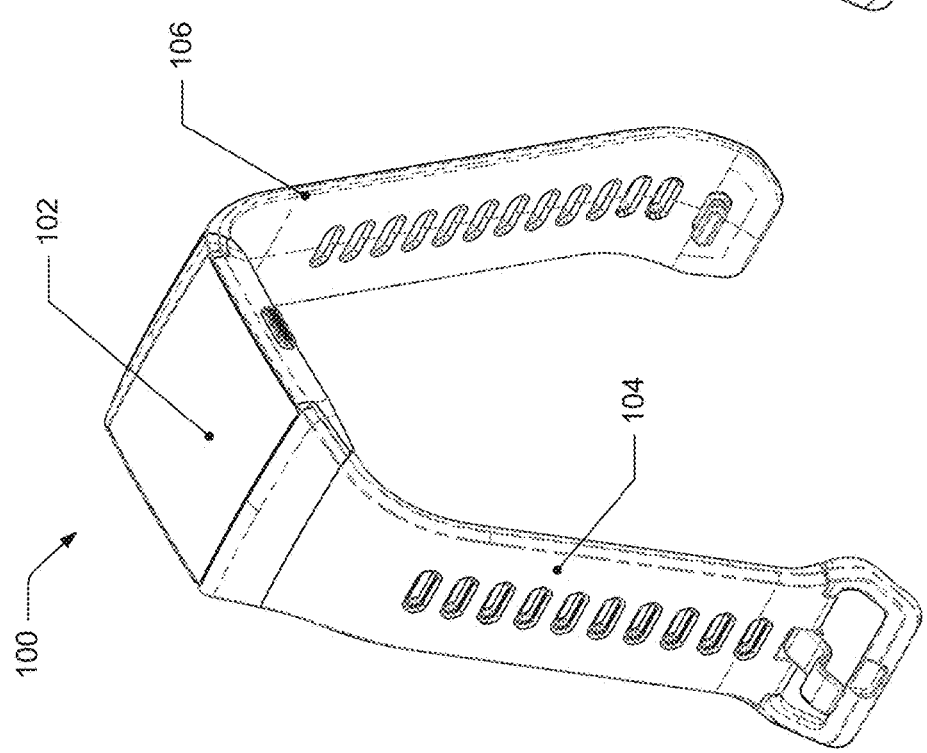
FIG. 1 depicts an isometric view of a fitness tracker.
Figure 3:
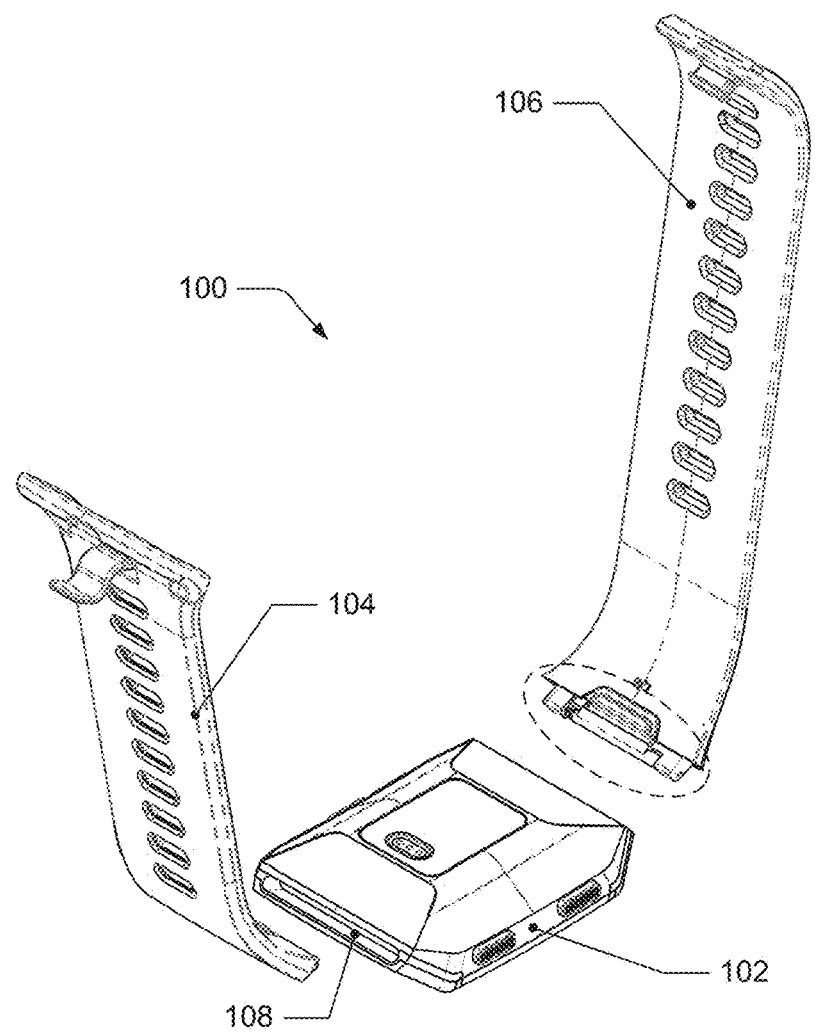
FIG. 3 depicts an exploded off-angle view of the fitness tracker of FIG. 1.

The disclosure herein includes a band latch mechanism that may be used for connecting a wristband strap to a housing of a fitness tracker. FIG. 1 depicts an isometric view of a fitness tracker, FIG. 2 depicts an exploded isometric view of the fitness tracker of FIG. 1, and FIG. 3 depicts an exploded off-angle view of the fitness tracker of FIG. 1. As can be seen in FIGS. 1-3, the fitness tracker 100 includes a housing 102, a first band portion 104, and a second band portion 106. As detailed below, the band latch mechanism is configured to be connected to one of the band portions, inserted into a cavity of the housing, and to connect the band latch mechanism to the housing. Some portions of the band latch mechanism that are configured to be inserted into the cavity and configured to connect to the housing are within with dashed ellipses in FIGS. 2 and 3.

Figure 4:
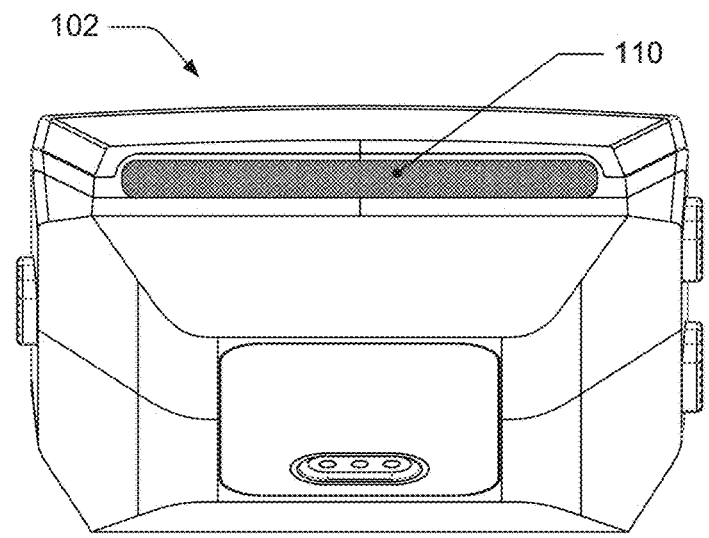
FIG. 4 depicts a view of the housing of the fitness tracker of FIG. 1 along a direction parallel to the direction of insertion for a strap of the fitness tracker.

The cavity 108 is identified in FIG. 3 and discussed in further detail in FIGS. 4-8. The cavity 108 has an opening and cavity walls that bound a representational volume of the cavity 108. The side walls of the cavity 108, not including the back of the cavity opposite the opening, are substantially parallel with each other (e.g., within +/−1% of parallel) such that when the band attachment mechanism is inserted into the cavity 108 along an insertion direction, the insertion direction is substantially parallel to the side walls of the cavity 108. The cross-sectional area of the representational volume in a plane perpendicular to the insertion direction has a shape that is generally rectangular with radiused corners. For instance, FIG. 4 depicts a view of the housing of the fitness tracker of FIG. 1 along a direction parallel to the direction of insertion for a strap of the fitness tracker. The housing 102 is oriented in this Figure such that the view is along the insertion direction of the cavity 108 and the opening 110 of the cavity 108 is identified with shading (the opening 110 also defines a cross-section of the representational volume). FIG. 5 depicts the cross-sectional area of the representational volume which has the generally rectangular shape that includes a length 114, a height 116, and a corner radius 118. In some embodiments, the length 114 may be substantially 28.8 millimeters, the height may be substantially 2.16 millimeters, and the radius may be substantially 0.80 millimeters. For these measurements, "substantially" means within +/−5% of such values.

FIG. 6 depicts an isometric view of the representational volume that is bounded by the cavity of the housing. The representational volume 120 that is bounded by the cavity 108 has a substantially constant cross-sectional area (identified in dark shading) along the insertion direction 122 (and may thus be considered substantially prismatic in shape) for a depth 124, such as at least 3.19 millimeters, for example. As discussed herein, portions of the band latch mechanism are configured to be inserted through the opening 110 and into the cavity 108 of the housing 102. In some instances, the cross-sectional area of the opening 110 of the cavity 18 may not be parallel to the cross-sectional area of the representational volume of the cavity 108. For instance, FIG. 7 depicts a partial cross-sectional side view of the housing. Here, the view is along a direction parallel to the planes in which the cross-sectional areas of the opening 110 and of the representational volume 120 have been taken; the cross-sectional area of the opening 110 of the cavity 18 is represented as line 710 and the cross-sectional area of the representational volume 120 of the cavity 108 is represented as line 708. Lines 710 and 708 are shown as nonparallel to each other with respect to the insertion direction 122. For some fitness trackers, the cross-sectional area of the opening 110, i.e., the surface that is defined by the inner edge of the opening, may not be parallel to the cross-sectional area of the representational volume 120 in a plane perpendicular to the insertion direction 122. Nonetheless, the band latch mechanism is configured to be inserted through the opening 110 and into the cavity 108 in such instances. The depth of the cavity 124 in FIG. 7 may, in some embodiments, measure at least 3.19 millimeters, and the distance 725 between the opening 110 and the boundary of the notch 112 closest to the opening 110 may be about 0.8 millimeters+0.02/−0.05 millimeters.

FIG. 8 depicts a different front view of the housing of the fitness tracker of FIG. 1. The housing 102 is oriented at a lower angle than in FIG. 4 and a notch 112 in the cavity 108 can be seen.

In some example implementations, the housing of the fitness tracker may include a metallic body that forms at least a part of the boundaries of the cavity 108 and a metallic antenna in close proximity to the cavity 108. Referring back to FIG. 7, the antenna 103 is located above the metallic body 105. While many internal aspects of the fitness tracker have been omitted from FIG. 7, a non-metallic material 107, such as a plastic, is seen separating the antenna 103 from the metallic body 105. It was discovered that the performance of the antenna decreased when metallic bodies were positioned within a particular threshold distance or zone from the antenna 103. This may be considered a "keep-out" zone which varies for different antennas. The metallic body 105 is positioned and shaped so that it is outside the keep-out zone of the antenna 103. Although the metallic body 105 is described as metallic, in some embodiments this aspect of the housing may not be metallic, but rather a polymer, a plastic, a composite, or other material that can form a portion of the housing with suitable strength and rigidity, for example. It was further discovered that when a metallic body was inserted into the cavity 108 and made contact with the metallic surface of the cavity 108, the inserted metallic body became an electric ground for the metallic body 105 which caused the inserted metallic body to be within the keep-out zone of the antenna 103 and adversely affected the performance of the antenna 103. However, it was discovered that if a metallic body was inserted into the cavity 108, is within the keep-out zone, but does not make contact with the metallic surfaces of the cavity 108, then the inserted metallic body does not adversely affect the performance of the antenna 103. Accordingly, some embodiments of the band latch mechanism disclosed herein are intended to be inserted into the cavity to enable a wristband to be connected to the housing without having a metallic body contact the metallic surfaces of the cavity while still maintaining an adequate connection to the housing and having sufficient robustness, resilience, and strength.

Figure 9:
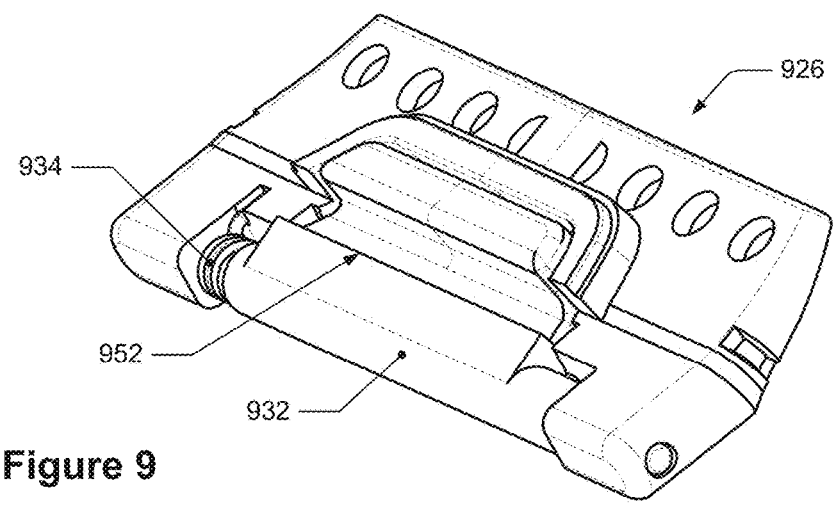
FIG. 9 depicts an off-angle view of an example band latch mechanism.
Figure 10:
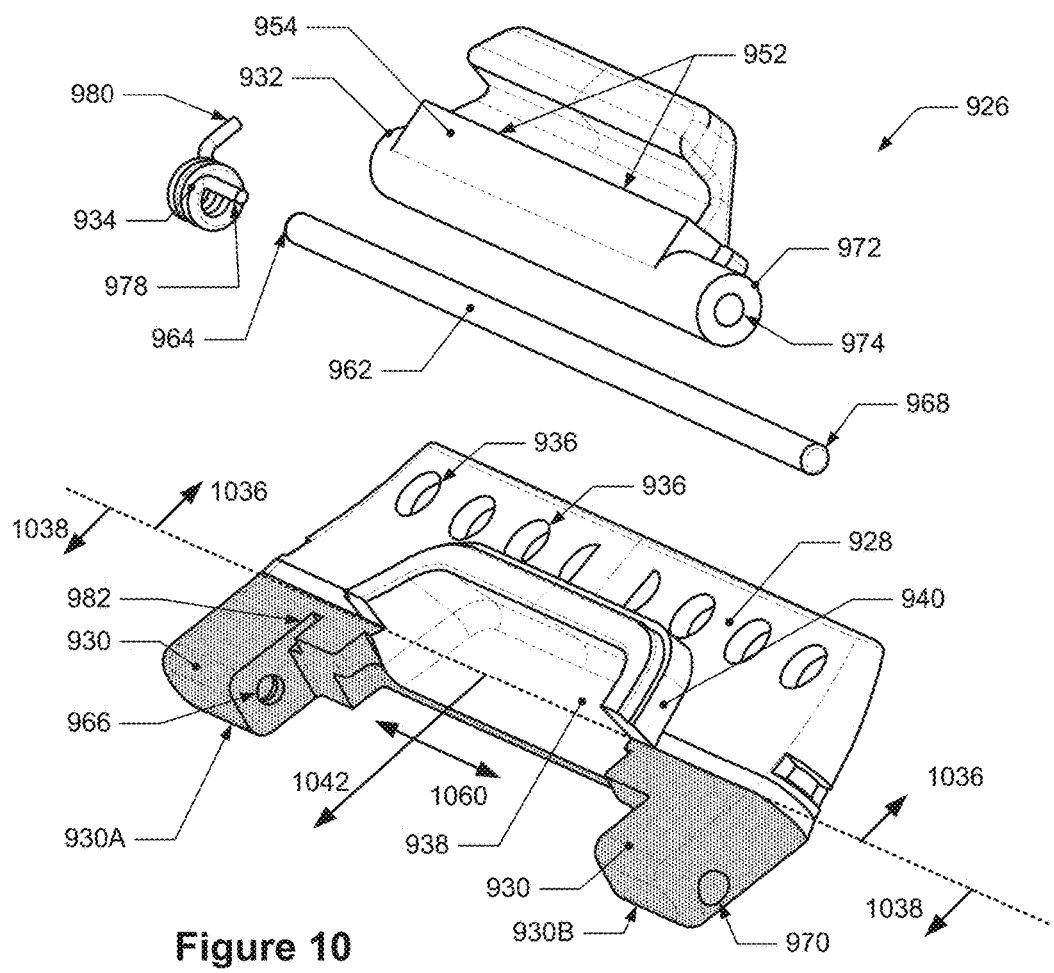
FIG. 10 depicts an exploded view of the band latch mechanism of FIG. 9.

FIG. 9 depicts an off-angle view of an example band latch mechanism and FIG. 10 depicts an exploded view of the band latch mechanism of FIG. 9. As can be seen in FIG. 10, the band latch mechanism 926 includes a body portion 928, an insertion portion 930, a latching portion 932, and a force biasing portion 934. The body portion 928 is seen on the side of the dashed line indicated by arrows 1036, while the insertion portion 930 is seen on the other side of the dashed line indicated by arrows 1038 and highlighted in shading.

In some embodiments, the body portion 928 is configured to be connected to a wristband, which may include having material and/or mechanical properties that enable it to connect with the wristband. For example, the body portion 928 includes a plurality of holes 936 that may be used to connect with a band during a molding or pressing manufacturing process; the body portion 928 may also be comprised of a polymer, composite, or other material that may be molded or pressed, etc.). In some embodiments, the body portion 928 may include mechanical features that enable it to connect with a band, such as protrusions and a pin that enable a fabric wristband to wrap around the pin and be secured to the body portion 928.

In some embodiments, the body portion 928 may also be a part or a component of the wristband itself. For example, the body portion 928 may be a contiguous component of the wristband that may be formed during the manufacturing process of the wristband. In some other embodiments, the body portion may be attached or affixed to the wristband, such as by an adhesive or bonding. Although described in greater detail below, the insertion portion 930 may be a contiguous element of the body portion and it may also be affixed or attached to the body portion 928, such as by mechanical features, an adhesive, or bonding.

Figure 11:
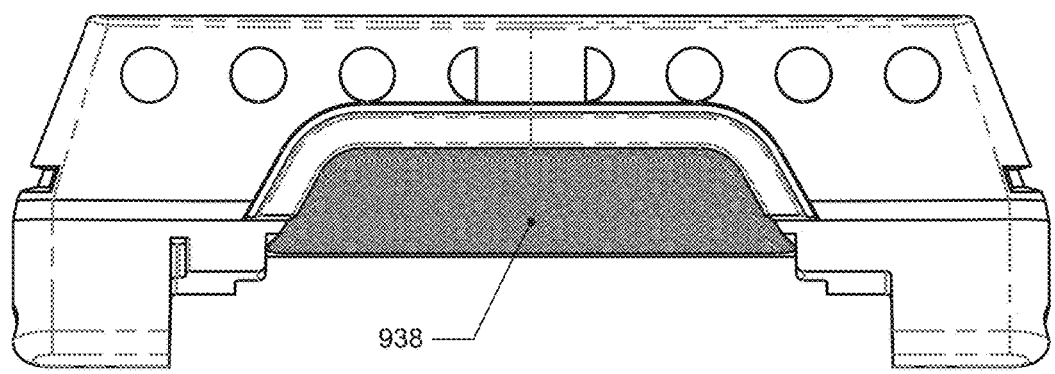
FIG. 11 depicts a top view of a body portion and an insertion portion of the band latch mechanism of FIG. 10.

The body portion 928 may also include a recess 938 that has a first cross-sectional area when viewed along a direction perpendicular to a top surface of the body portion 928. FIG. 11 depicts a top view of a body portion and an insertion portion of the band latch mechanism of FIG. 10. Here, the recess 938 has a first cross-sectional area that is shaded. The shape of the recess 938, including its first cross-sectional area and depth, is configured to permit movement of the latching portion within the recess as described below. The recess may extend partially through the body portion 928 and in some embodiments, it may extend fully through the body portion 928.

The body portion 928 may also include a wall 940 that extends around a part of the recess 938 and forms a part of the recess 938 as seen in FIGS. 10 and 11. The wall 940 may improve the structural integrity of the band latch mechanism 126 after insertion into the cavity. During a molding process of a polymer band material around the band latch mechanism, the wall may 940 prevent such band material from entering the recess 938. The wall 940 may also prevent flash from occurring.

Some embodiments of the insertion portion 930 will now be discussed. The insertion portion 930 is configured to be inserted into the cavity 108 of the fitness tracker 100; this configuration of the insertion portion 930 includes having a shape and size that fits through the opening 110 of the cavity 108 and into and within the cavity 108, including within the representational volume 120 of the cavity 108 described above. In order to do so, in some embodiments the insertion portion 930 is considered to be contained within and/or circumscribed by a prismatic reference volume that, in some embodiments, is circumscribed by the representational volume 120 of the cavity 108. In some embodiments, at least some portions of the insertion portion 930 may be considered contacting the outer boundary of the prismatic reference volume. Additionally, the prismatic reference volume may be understood to be a volume that is either the same as the representational volume 120 or that has exterior surfaces that are offset inwards from the representational volume 120 by a non-zero distance, such as about 0.02 millimeters or about 0.22 millimeters.

Figure 12:
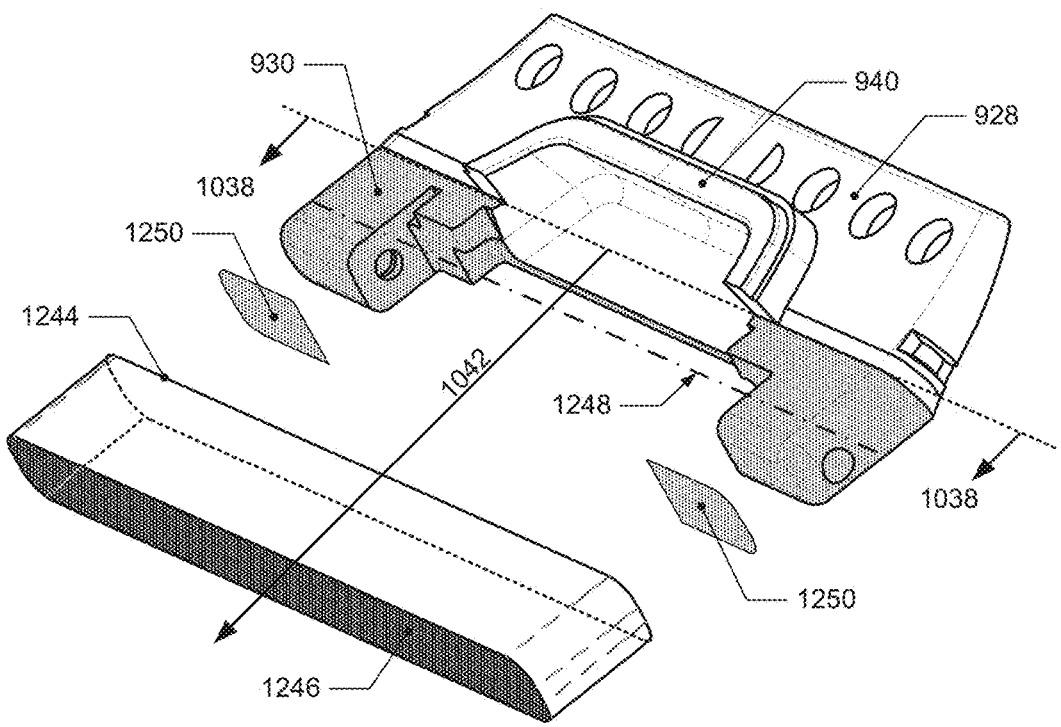
FIG. 12 depicts the body portion and the insertion portion of FIG. 10 and a prismatic reference volume.
Figure 13:
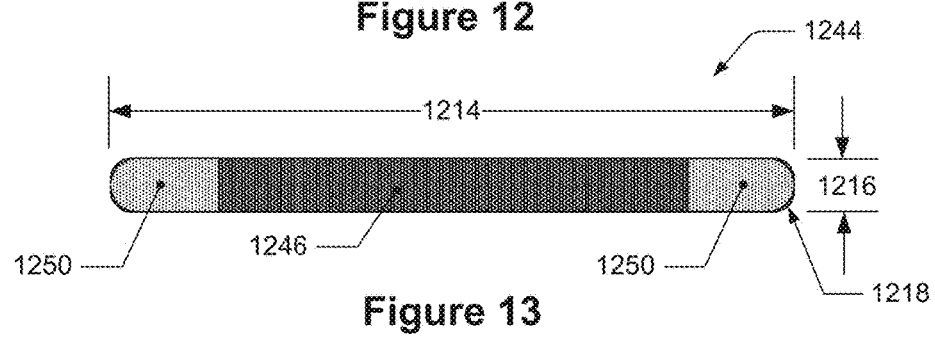
FIG. 13 depicts a second cross-sectional area of the prismatic reference volume along a first direction.

For example, in FIG. 12, which depicts the body portion and the insertion portion of FIG. 10 and a prismatic reference volume, the insertion portion 930 is seen extending away from the body portion 928 in the first direction 1042. In some embodiments, the body portion 928 is contiguous with the insertion portion 930, like in FIG. 12. In some other embodiments, as noted above, the body portion 928 and the insertion portion 930 may be separate bodies that are connected together, such as by an adhesive or other connector, like screws or bolts. The prismatic reference volume 1244 is shown separated from the band latch mechanism for clarity, but the prismatic reference volume 1244 is considered to contain the insertion portion 930 and to extend away from the body portion 928 in the first direction 1042. The prismatic reference volume 1244 has a second cross-sectional area 1246, identified with dark shading, that is in a plane perpendicular to the first direction 1042. FIG. 13 depicts the second cross-sectional area of the prismatic reference volume along the first direction. The shape of the second cross-sectional area 1246 is a rectangular shape like that of the cross-sectional area of the cavity 108 in a plane perpendicular to the insertion direction 122, i.e., the cross-sectional area of the representational volume 120, with a length 1214, a height 1216, and corners with a radius 1218. In some embodiments, the length 1214 of the second cross-sectional area 1246 is substantially 26.8 millimeters, the height 1216 of the second cross-sectional area 1246 is substantially 2.1 millimeters+0.09/−0.05 millimeters, and radius 1218 of the corners of the second cross-sectional area 1246 are substantially 0.80 millimeters. "Substantially" means within +/−5% of the values. In some such embodiments, the length of the insertion portion is substantially 26.6 millimeters, the thickness is substantially 2 millimeters; it may also have a length in the first direction 1042 that is substantially 3.1 millimeters. "Substantially" here means within +/−5% of the values.

The outer boundary of the second cross-sectional area 1246 circumscribes, or extends around, the outer boundary of the insertion portion 930 in a plane perpendicular to the first direction 1042. For example, when viewed along the first direction, the cross-sectional area of the insertion portion 930 in a plane perpendicular to the first direction 1042 is contained by the second cross-sectional area 1246. In some embodiments, the boundary of the second cross-sectional area 1246 may circumscribe at least some parts of the cross-sectional area of the insertion portion 930 in a plane perpendicular to the first direction such that, for instance, at least some parts of the cross-sectional area of the insertion portion are touching the second cross-sectional area 1246. Referring back to FIG. 12, a cross-sectional slice of the insertion portion 930 has been taken in a plane perpendicular to the first direction 1042 along line 1248 and is identified with light shading and identified 1250. FIG. 13 also depicts the cross-sectional slice 950 of the insertion portion 930 and as can be seen, this cross-sectional slice, i.e., a third cross-sectional area of the insertion portion 930, includes two separated areas which together are contained within the second cross-sectional area 1246. Other cross-sectional areas (not shown) of the insertion portion 930 are likewise contained within the second cross-sectional area 1246; in other words, these other cross-sectional areas are circumscribed by the boundary of the rounded-corner shape of the second cross-sectional area 1246.

In some embodiments, the cross-sectional areas of the insertion portion may be of a different shape than shape depicted in the Figures, but may nonetheless still be considered contained within, and in some embodiments circumscribed by, the rounded-corner shape of the prismatic reference volume 1244. For instance, the insertion portion 930 may have a cross-sectional shape that includes square-corners or that may be a circle, but the cross-sectional shape is still sized and configured such that it is contained within, or even circumscribed by, the rounded-corner shape of the prismatic reference volume 1244.

Figure 14:
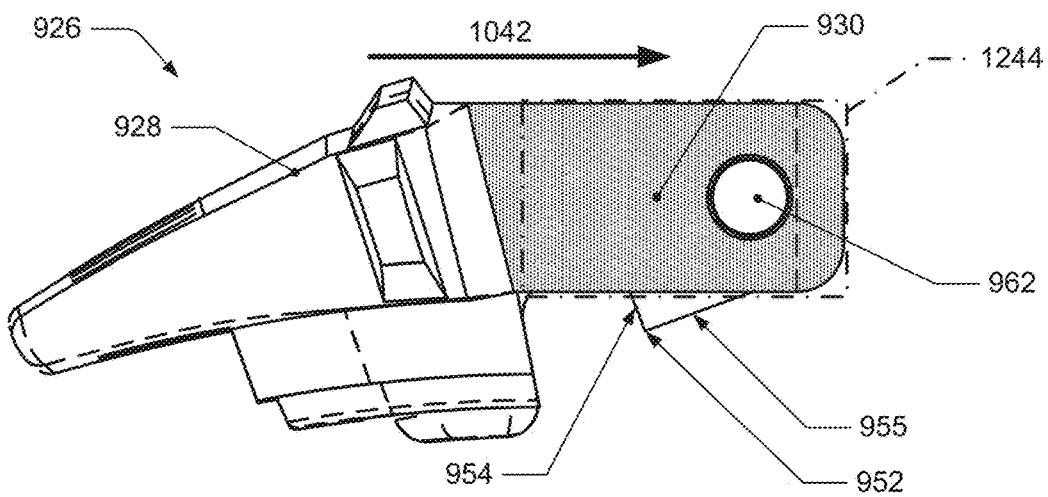
FIG. 14 depicts a side view of the band latch mechanism of FIG. 9.

Some embodiments of the latching portion 932 will now be discussed. The latching portion has an edge that is configured to latch with and connect to the notch of the housing; the edge may also be referred to as a "latching edge." The latching edge is configured to be moveable, i.e., displaceable, between at least two positions such that the latching edge may move through the opening of the cavity and into the notch of the cavity. The latching edge 952 can be seen in FIGS. 9 and 10. Additionally, FIG. 14 depicts a side view of the band latch mechanism of FIG. 9 which is a view along the latching edge. As can be seen, the insertion portion 930 (shaded) extends in the first direction 1042 and is contained within the prismatic reference volume 1244 which is represented as a dash-dot-dash boundary line. The latching edge 952 of the latching portion 932 is seen outside this prismatic reference volume 1244. In some embodiments, like that in FIG. 14, the latching portion 932 may include a first surface 954 and a second surface 955 that intersect to form the latching edge 952. The internal angle between the first surface 954 and the second surface 955 may be about 95 degrees or less.

Figure 15:
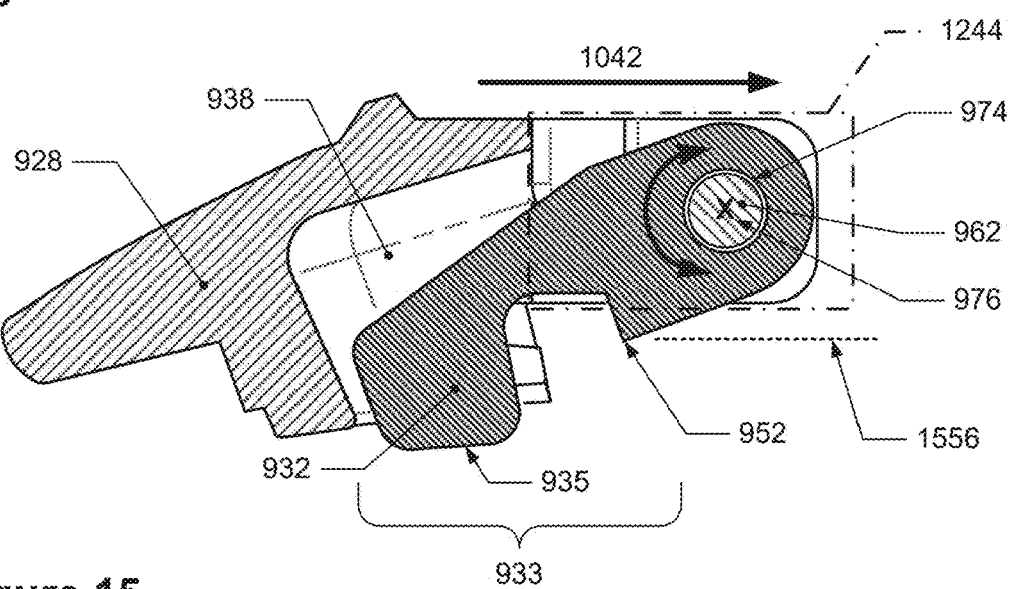
FIG. 15 depicts a cross-sectional side view of the band latch mechanism of FIG. 14 with a latching edge of a latching portion in a first position.
Figure 16:
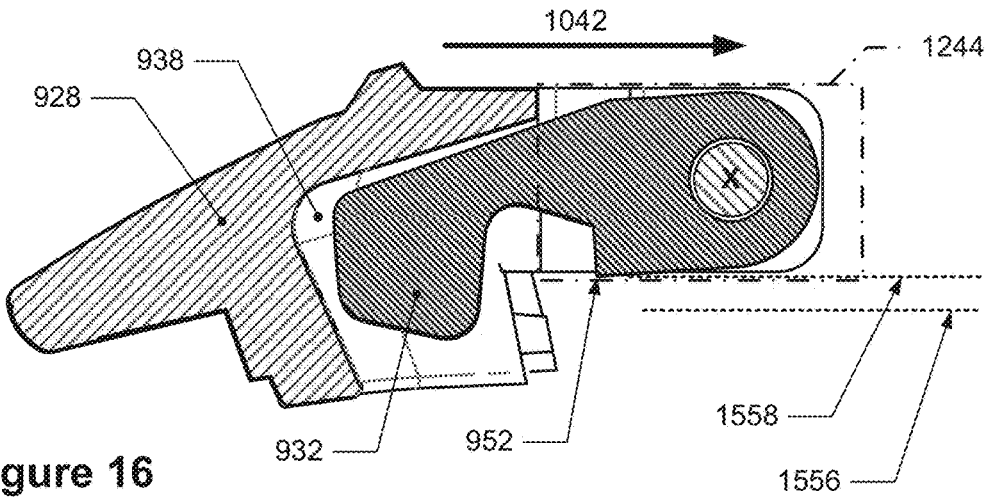
FIG. 16 depicts a cross-sectional side view of the band latch mechanism of FIG. 14 with the latching edge of the latching portion in a second position.

FIG. 15 depicts a cross-sectional side view of the band latch mechanism of FIG. 14 with the latching edge of the latching portion in a first position while FIG. 16 depicts a cross-sectional side view of the band latch mechanism of FIG. 14 with the latching edge of the latching portion in a second position. In FIG. 15, the cross-section has been taken in a plane along a centerline of the band latch mechanism in a direction parallel to the first direction 1042 and perpendicular to a rotational axis of the latching portion. The recess 938 of the body portion 928 can be seen and a part of the latching portion 932 is positioned within the recess 938. The latching edge 952 of the latching portion 932 is seen at a first position 1556, which is represented by the horizontal dashed line parallel to the first direction 1042. As can be seen, when the latching edge 952 is in the first position 1556, the latching edge 952 is located outside the boundary of the prismatic reference volume 1244 and may also be considered outside the representational volume 120 of the cavity 108.

In FIG. 16, the latching portion 932 has moved such that the latching edge 952 is in the second position 1558, which is represented by the horizontal dashed line parallel to the first direction 1042. When in the second position 1558, the latching edge 952 is located within the prismatic reference volume 1244 which enables the insertion portion 1530 and the part of the latching portion 1532 that includes the latching edge 952 to be inserted into the cavity 108. The displacement of the latching edge 952 between the first position 1556 and the second position 1558 may be considered to be in a direction perpendicular to the first direction 1042. As can also be seen in FIG. 16, the recess 938 is configured to permit the movement of the latching portion 932 such that more of the latching portion 932 is located within the recess 938 when the latching edge 952 is in the second position 1558.

The band latch mechanism 926, including the latching portion 932, may be configured in a variety of ways in order to have the latching edge move between positions, including the first position and the second position. In some embodiments, the latching portion of the band latch mechanism may be rotatably connected to the body portion and/or the insertion portion such that the latching portion is rotatable about a rotation axis and which in turn moves the latching edge between at least the first position and the second position. For example, in the embodiment shown in FIGS. 9-16, the latching portion 932 is rotatably connected to the insertion portion 930 and the insertion portion 930 is configured for such connection.

For example, in FIG. 10 the insertion portion 930 includes a first protrusion 930A and a second protrusion 930B which are offset from each other in a direction 1060 that is perpendicular to the first direction 1042 so that a gap exists between each protrusion. The band latch mechanism 926 may also include a pin which extends through the latching portion, is positioned within each protrusion of the insertion portion, and is the physical member about which the latching portion rotates (or that defines the center axis about which the latching portion rotates). A pin 962 can be seen in the exploded view of FIG. 10. When assembled, a first end 964 of the pin 962 is positioned in a first hole 966 of the first protrusion 930A and a second end 968 of the pin 962 is located in a second hole 970 of the second protrusion 930B. The latching portion 932 also includes a latching body 972 that has a latching hole 974 that extends through the latching body 972. When the band latch mechanism is assembled, the pin 962 extends through the latching hole 974 and the latching portion 932 rotates around the pin 962. The latching portion 932 rotates about a rotation axis which extends between the first protrusion 930A and the second protrusion 930B. The rotation axis may be located in various positions, such as collinear with the center axis of the latching hole 974, collinear with the center axis of the pin 962, parallel to but offset from the center axis of the pin 962, and/or parallel to the center axis of the pin 962.

Viewed from a different perspective, in FIGS. 14 and 15 the pin 962 is seen positioned within the latching hole 974. The rotation axis, which is shown as an "x" and identified with 976, is collinear with both the center axis of the pin 962 and the center axis of the latching hole 974. The latching portion 932 rotates about pin 962, as indicated by the curved double-sided arrow, thereby causing the latching edge 952 to move between the first position 1556 and the second position 1558. In some embodiments, the rotational distance between the first position and the second position is substantially 20 degrees. Here, "substantially" means within +/−10% of the value.

The band latch mechanism may also include a force biasing portion, such as a spring, that is configured to apply a force to the latching portion to enable the latching portion to move between multiple positions when subjected to an external force, e.g., pressure applied by a user's finger, and return to a starting position when the external force is released. The configuration of the force biasing portion causes the latching edge of the latching portion to move into and remain within the notch of the cavity of the housing, thereby causing the band latch mechanism to be connected with the housing. For example, referring to FIGS. 15 and 16, a force biasing portion exerts a force onto the latching portion 932 which causes the latching portion to remain in the first position 1556, but when an external force that is greater than the force applied by the force biasing portion is applied to the latching portion, such as a force by a user onto the latching portion, the latching portion 932 is caused to move to the second position 1558, albeit under resistance applied by the force biasing portion. Once the external force is no longer applied to the latching portion 932, the force biasing portion causes the latching portion 932 to return to the first position 1556. The force biasing portion may be any suitable material and configuration that applies a force to and enables the movement of the latching portion as described herein, e.g., enables the movement of the latching portion between multiple positions when subjected to an external force and return to a starting position when the external force is released. For instance, the force biasing portion may be a spring, a torsional spring, a hinge, or elastically deformable material such as rubber; the force biasing portion may also be a metal, polymer, plastic, composite, polycarbonate, or other suitable material.

For example, in some embodiments, the latching portion 932 may include a latching lever that is connected to the latching edge. A section 933 in FIG. 15 may be considered the latching lever 933 which is connected to the latching edge 952. The latching lever 933 is configured to cause, when a force is applied to a button surface 935 of the latching lever 933, the displacement of the latching edge 952 from the first position 1556 to another position between and including the second position 1558. When the latching edge 1552 has been displaced from the first position and moved to another position, such the second position 1558, and the force of the user is removed from the latching lever 933, then the force biasing portion 934 causes the latching edge 952 to move back to the first position 1556 (assuming that no other body obstructs this movement).

Additionally, referring back to FIGS. 9 and 10, the depicted force biasing portion 934 of the band latch mechanism 926 is a 90 degree tangential torsion spring (referred hereinafter as "spring 934") that is wrapped around the pin 962. The spring 934 has a first end 978 that is connected to the latching portion 932, such as by being inserted into another hole in the latching portion 932, affixed to the latching portion (e.g., by an adhesive), or being molded into the latching portion 932. The spring 934 also has a second end 980 that contacts the insertion portion 930 or the body portion 928, such as a second recess 982 of the body portion 928. The spring 934 is thereby configured to apply a rotational spring force that enables latching portion 932 to rotate about a rotational axis as well as return to a starting position. In some embodiments, the torsion spring 934 may have four active coils, a mean coil diameter of substantially 1.35 millimeters, a wire diameter of substantially 0.35 millimeters, and a deflection angle of at least 20 degrees. "Substantially" here means within +/−10% of the listed values.

The latching lever 933 may also be configured to fit within the prismatic reference volume 1244 so that it may be inserted into the cavity 108. As can be seen in FIGS. 15 and 16, for example, the cross-sectional area of the latching lever 933 in a plane perpendicular to the first direction 1042 is less than the cross-sectional area of the cavity 108 in a plane along the insertion direction and of the prismatic reference volume 1244. Additionally, the latching lever 933 is configured to fit within the recess 938 so that the latching lever 933 and latching portion 932 may move within the recess as described above. In some such embodiments, the latching lever 933 has a fourth cross-sectional area in a plane parallel to the first direction that is less than, or fits within, the first cross-sectional area of the recess 938.

Figure 17A:
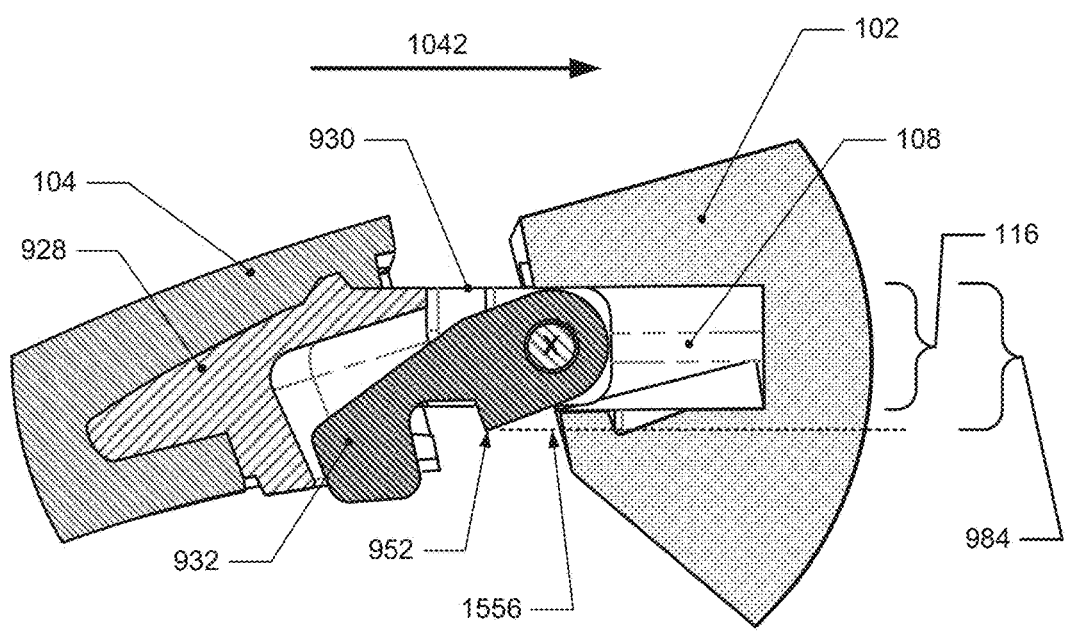
FIGS. 17A-17D depict cross-sectional side views of an example insertion sequence of the band latch mechanism into the housing.

The above-described movements and configurations of the band latch mechanism enable the insertion portion and the latching portion to be inserted into the cavity and for the band latch mechanism to be attached to the housing. For instance, FIGS. 17A-17D depict cross-sectional side views of an example insertion sequence of the band latch mechanism into the housing. In these Figures, the body portion 928 has been connected to a band portion 104. In FIG. 17A, the band latch mechanism in positioned like in FIG. 15 such that the latching edge 952 of the latching portion 932 is in the first position 1556 as caused by the force biasing portion (not seen). In some embodiments, when the latching edge 952 is in the first position 1556, the force biasing portion, such as the spring 934, may be deflected by a first amount, which may include zero. Some of the insertion portion 930 and the latching portion 932 have been moved through the opening of cavity 108 and into the cavity 108 in the first direction 1042 (which may also be considered the insertion direction 122). As can be seen, with the latching edge 952 in the first position 1556, the latching portion 932 prevents the insertion of the band latch mechanism fully into the cavity 108. In some such embodiments, like can be seen in FIG. 17A, a first effective height 984 of the latching portion 932 measured between a top surface of the latching portion 932 and the latching edge 952 in a direction perpendicular to the first direction 1042 is larger than the height 116 of the opening 110 as well as the height of the cavity. The cross-sectional area of the latching portion 932 in a plane perpendicular to the first direction 1042 while the latching edge 952 is in the first position 1556 may also be considered larger than the cross-sectional area of the opening 110.

Figure 17B:
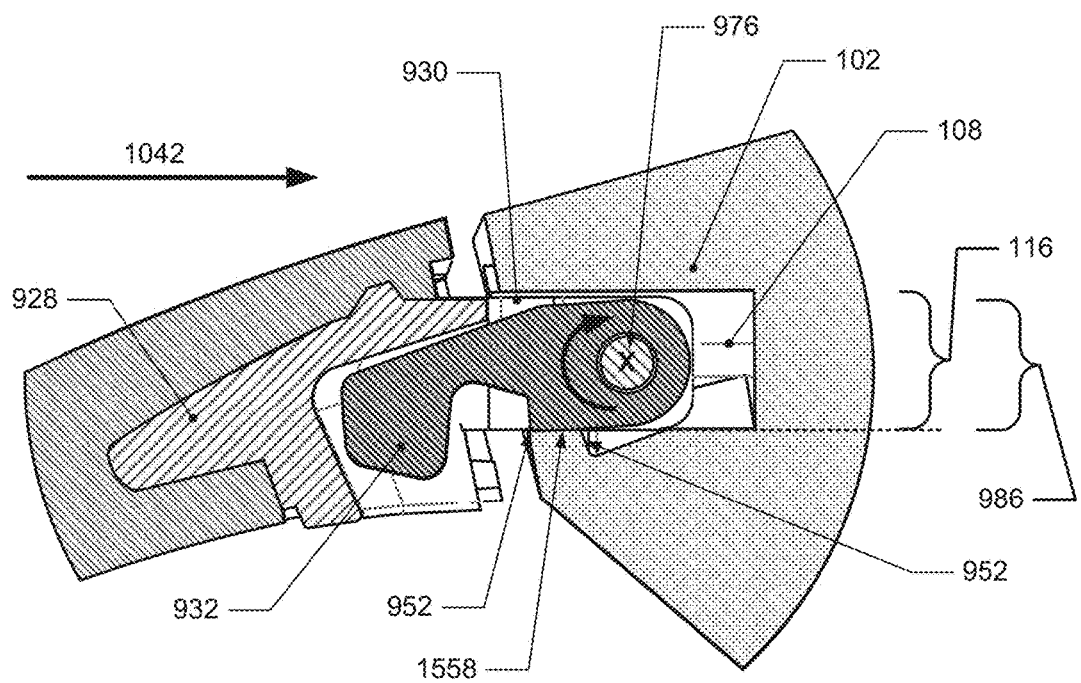

When a force is applied to the latching portion, such as by a user directly on the latching portion or a user moving the insertion portion into the cavity, that is greater than the spring biasing force, then the latching edge can be moved in to the second position and the band latch mechanism can be inserted farther into the cavity like in FIG. 17B. Here, the band latch mechanism in positioned like in FIG. 16 such that the latching edge 952 of the latching portion 932 is in the second position 1558. More of the insertion portion 930 and the latching portion 932 have been moved through the opening of cavity 108 and into the cavity 108. The movement of latching portion 932 so that the latching edge 952 is in the second position 1558 enables the latching edge 952 and more of the latching portion 932 and the insertion portion 930 to move through the opening and into the cavity 108. Like described above, in FIG. 17B the latching portion 132 has rotated clockwise about the rotational axis 976 as indicated by the arrow thereby causing the latching edge 952 to move from the first position 1556 to the second position 1558. In some such embodiments, like in FIG. 17B, when the latching edge 952 is in the second position 1558, a second effective height 986 of the latching portion 932 measured between a top surface of the latching portion 932 and the latching edge 952 in a direction perpendicular to the first direction 1042 is less than the height 116 of the opening 110 as well as the height of the cavity. Additionally, when the latching portion 932 is in the second position 1558, the force biasing portion, such as spring 934, is deflected by a second amount that is greater than the first amount.

Figure 17C:
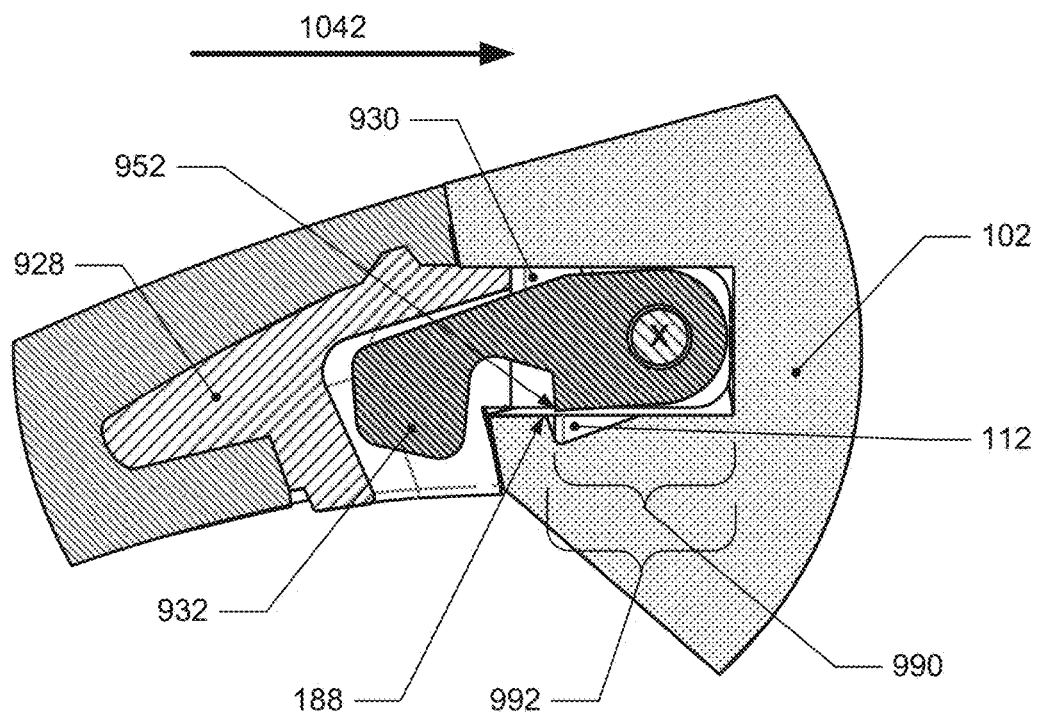
Figure 17D:
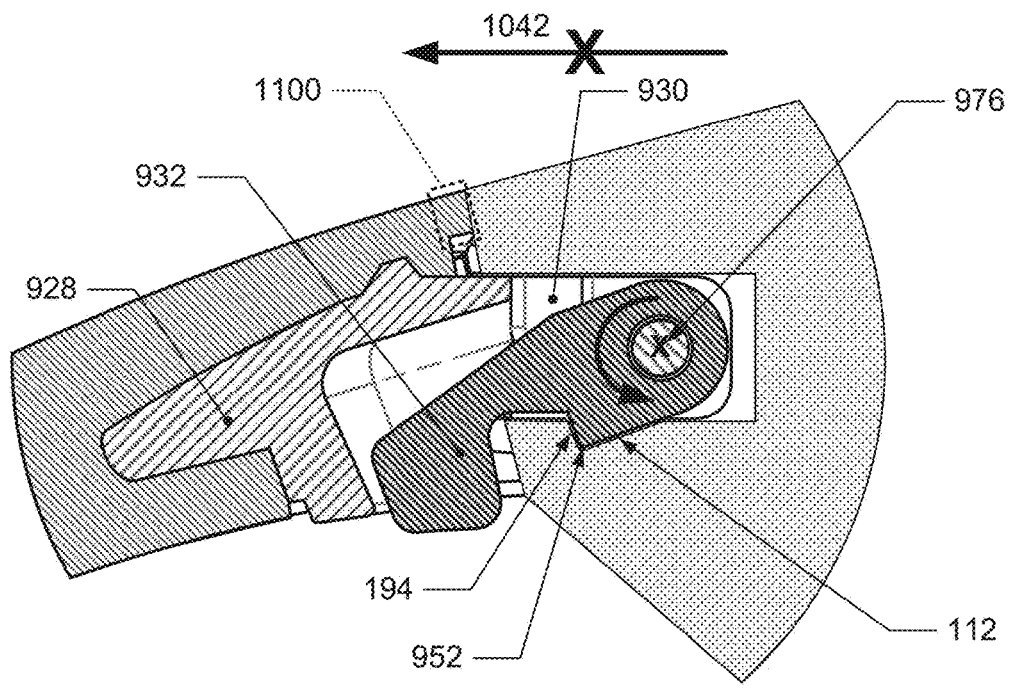
Figure 18:
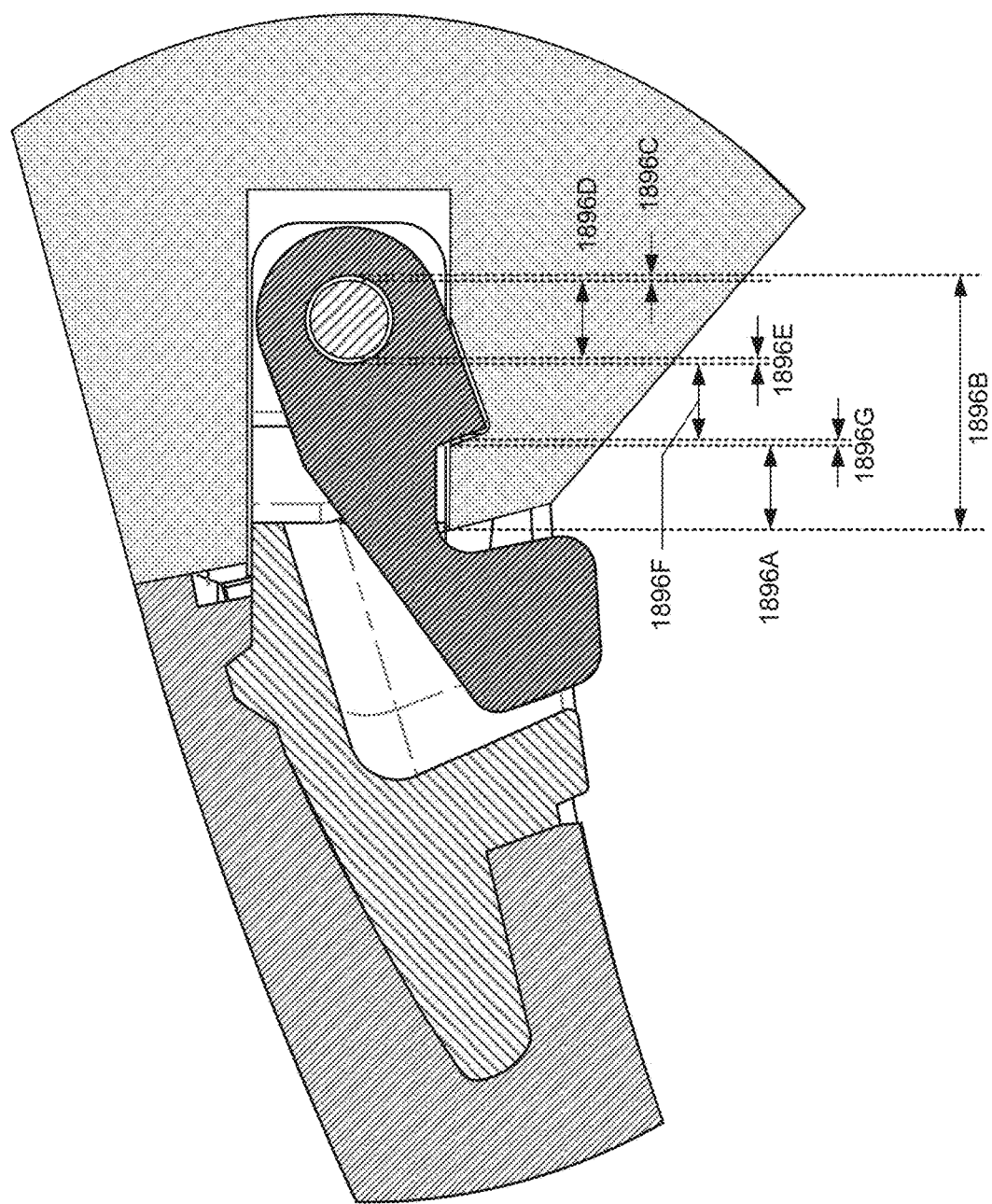
FIG. 18 depicts the cross-sectional side view of the band latch mechanism inserted into the housing like in FIG. 17D.

In FIG. 17C, the band latch mechanism has been moved farther into the cavity 108 in the first direction 1042 so that the latching edge 952 may be positioned within the notch 112 like in FIG. 17D. In order for the latching edge 952 to be positioned within the notch 112, the insertion portion 930 and the latching portion 132 are sized so that the latching edge 952 can move in the first direction 1042 past a section of the notch boundary 188 that is closest to the opening and then move in a direction with a component perpendicular to the first direction 1042 and into the notch 112. For example, in some embodiments, the depth 990 of the insertion portion 930 in the first direction 1042 as measured between the front surface of the insertion portion 132 and the latching edge 152 when the latching edge 952 is in the second position 1558 is less than a distance 192 between the end of the cavity 108 and the notch boundary 188. Some example measurements are provided in FIG. 18 below.

In FIG. 17D, the latching edge 952 is positioned within the notch 112 of the cavity 108 of the housing 102. Like described above, the force biasing portion (not seen) has caused the latching portion 132 to rotate in a counter clockwise direction about the rotational axis 976, as indicated by the curved arrow, so that the latching edge 952 is forced to be within the notch 112. The band latch mechanism has also been moved in the first direction 1042 as indicated by the arrow 1042, e.g., towards the left of the Figure and towards the opening of the cavity. In some embodiments, like that shown in FIG. 17D, the first surface 954 of the latching portion 132 may engage with a notch surface 194 of the notch 112 (also identified in FIG. 17B) which prevents the band latch mechanism from being removed from the cavity, such as when a force is applied to the band latch mechanism and/or band in the first direction 1042 as indicated in FIG. 17D. In some embodiments, when the latching edge is located within the notch 112 of the cavity 108, the latching edge 952 may be located in the first position 156 as well as in other positions between the first position 156 and the second position 158.

As mentioned above, the size and shape of the insertion portion and the latching portion are configured to fit within the cavity of the housing so that the latching edge of the latching portion may be positioned within the notch. Such configuration includes, for example, the measurements described above as well as those shown in FIG. 18 which depicts the cross-sectional side view of the band latch mechanism inserted into the housing like in FIG. 17D. As can be seen, various dimensions 1896A-1896G are provided: 1896A is the distance between the opening of the cavity and the notch, 1896B is the edge of the opening of the cavity to the edge of the holes in the insertion portion, 1896C is the gap between the pin and the holes in the insertion portion, 1896D is the pin diameter, 1896E is the gap between the pin and the hole in the latching portion, 1896F is the distance between the hole in the latching portion and the first surface of the latching portion, and 1896G is the gap between the notch surface and the first surface of the latching portion. For clarity, only these items are identified in FIG. 18; the other depicted items have been previously identified. In some embodiments, 1896A is 0.72 millimeters+/−0.25 millimeters, 1896B is 2.47 millimeters+/−0.05 millimeters, 1896C is 0 millimeters+/−0 millimeters, 1896D is 0.8 millimeters+/−0.03 millimeters, 1896E is 0.05 millimeters+/−0.1 millimeters, 1896F is 0.85 millimeters+/−0.04 millimeters, and 1896G is 0.05 millimeters+/−0.370 millimeters. Additionally, a distance 1896I between the center of the hole of the latching portion 932 and the latching edge 952 may be substantially 1.53 millimeters. In some embodiments, the configuration of the band latch mechanism, including the aforementioned measurements, may result in a space 1896J (which may also be distance 1896H, discussed below) between the front of the insertion portion 930 and the back wall of the cavity 108 and between the end of a rib 1100, discussed below, and the band 106 which also results in a tolerance in the insertion direction 1042, both of which enable the band latch mechanism to be inserted into the cavity 108 and latch to the housing 102. In some embodiments, the space 1896J is substantially 0.35 millimeters and the tolerance is substantially 0.16 millimeters. "Substantially" herein means within +/−5%.

In some of the embodiments in which the band latch mechanism includes one or more metallic surfaces, the band latch mechanism is configured so that none of the metallic surfaces contact the metallic surfaces of the cavity 108 of the housing 102. For example, referring back to FIGS. 9 and 10, the insertion portion 930 and the latching portion 932 may both be comprised of one or more non-metallic materials, such as a polymer, thermoplastic polymer, polycarbonate, composite, or other material that enables the insertion portion 930 and the latching portion 932 to be configured, insertable, and moveable as described herein. In some other embodiments, the insertion portion 930 and the latching portion 932 may be made of a metallic material but coated with a non-metallic coating so that the exterior surfaces of these portions are non-metallic. Additionally, in some embodiments, the exterior surfaces of the insertion portion 930 and the latching portion 932 that contact any portion of the metallic surfaces of the cavity 108 may be comprised of a non-metallic material. Similarly, the body portion 128 may also be comprised of a non-metallic material and may also have exterior surfaces that are non-metallic.

The pin 962 and/or the force biasing portion 934 shown in FIGS. 9 and 10 and discussed above may, in some embodiments, be comprised of a metallic material, such as stainless steel or steel. In some embodiments, the pin and/or the force biasing portion may be comprised of a non-metallic material, such as a polymer, plastic, or polycarbonate, or any other material that may enable the latching portion to be rotatable and moveable as described herein. In such embodiments, the band latch mechanism is configured so that any metallic surface of pin 962 and the force biasing portion 934 do not contact any of the metallic surfaces of the cavity of the housing. For example, such configuration includes the force biasing portion 934 and the pin 962 both being contained within the prismatic reference volume 944. As can be seen in FIG. 9, for instance, the pin 962 does not extend beyond the outer boundary of the insertion portion 930. Similarly, in FIGS. 17A-17D, the spring 934 is not seen because it does not extend outside the prismatic reference volume. FIGS. 19B, 19D, and 19F also show the pin 962 (not labeled) and the spring 934 not extending past the outer boundaries of the insertion portion and not extending outside the prismatic reference volume (not shown).

As stated above, the body portion of the band latch mechanism may be connected to a band as illustrated in FIGS. 19A-19F. FIG. 19A depicts a front view of the band latch mechanism connected to a wristband of FIG. 2, FIG. 19B depicts a detail view of FIG. 19B, FIG. 19C depicts an off-angle view of the band latch mechanism of FIG. 19A, FIG. 19D depicts a detail view of FIG. 19C, FIG. 19E depicts another off-angle view of the band latch mechanism of FIG. 19A, and FIG. 19F depicts a detail view of FIG. 19E. In FIGS. 19A-19F, the body portion is embedded within the band 106, which is the second band portion of FIGS. 1-3.

As can also be seen in these Figures, the insertion portion 930 extends out and away from the band 106. In some embodiments, the band includes a band body portion 1998 and a rib 1100 that extends from the band body portion 1998, as identified with shading in FIGS. 19B and 19D, for example. In some embodiments, the rib 1100 extends around a section of the body portion, the latching portion, and/or the insertion portion. For instance, as can be seen in FIG. 19B, which is a view along the first direction, the rib 1100 extends around some of the body portion (not shown), the latching portion 932, and the insertion portion 930, but not fully around these portions at this angle. This allows for the movement of the latching portion 132 as described above.

In some embodiments, the rib 1100 may also be comprised of a compliant material, such as an elastomeric polymer, rubber, or fabric, or any other material that allows it to be compressed as described herein. The compliance, or compressibility, of the rib 1100 may assist in securing the band latch mechanism and band to the housing. For instance, referring back to FIG. 17D, the rib 1100 is located within the dashed rectangular box. The presence of the rib 1100 may provide a force against the housing that causes the latching portion 132 to be secured to the housing with limited to no movement or slack when the latch portion is engaged with the notch. In some embodiments, the force of the rib 1100 is due to the rib 1100 being compressed during the insertion of the band latch mechanism into the housing, like can be seen in FIG. 17C; it may then remain in a less-compressed state after the insertion and the latching edge 952 is in the notch 112, such as depicted in FIG. 17D. In some embodiments, the rib may be compressible by at least substantially 0.03 millimeters. Referring back to FIG. 18, in some embodiments the rib 1100 may have a depth 1896H of substantially 0.35 millimeters ("substantially" here means within +/−5%).

Figure 20:
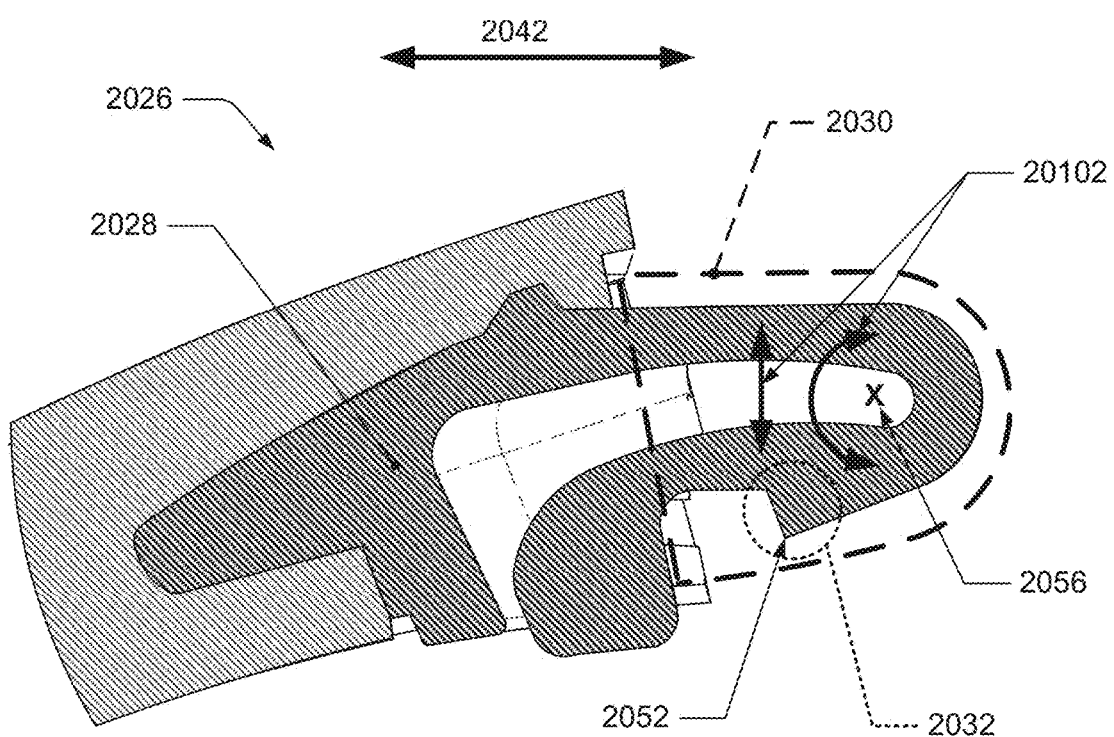
FIG. 20 depicts a cross-sectional view of an example band latch mechanism having a contiguous body portion, insertion portion, and latching portion.

In other embodiments, the latching portion may be contiguous with the insertion portion, as well as contiguous with the body portion. For example, FIG. 20 depicts a cross-sectional view of an example band latch mechanism having a contiguous body portion, insertion portion, and latching portion. As can be seen, the body portion 2028, the insertion portion 2030, and the latching portion 2032 are one single, unitary body. Here, the latching portion 2032, identified within the dotted-line circle and having the latching edge 2052, is a part of the insertion portion 2030, which is contained within the dashed-line shape. Similar to described above, the band latch mechanism 2026 is configured so that the latching edge 2052 is displaceable between the first position and the second position, but here, the body portion 2028, insertion portion 2030, and latching portion 2032 are comprised of an elastically deformable material and shaped to enable movement of the latching portion 2032 so the latching edge 2052 can be in the first and second positions like described above. This elasticity of the material and the shape of this band latch mechanism 2026, such as the insertion portion 2030 and the latching portion 2032, are the force biasing portion which causes the latching edge 2052 to return from the second position to the first position and other positions in-between. For instance, the insertion portion 2030 may move during the displacement of the latching portion 2032 and the latching portion 2032 may be rotatable about a rotation axis and also displaceable along an axis perpendicular to the first direction 2042, as indicated by the two directional arrows 20102 in FIG. 20.

As discussed earlier, the band latch mechanisms (and bands) discussed above may be connected with a biometric monitoring device, e.g., a device that includes one or more biometric sensors and that is configured to obtain data regarding one or more physiological or biometric aspects of the wearer. Such devices may include a housing that contains the various components that provide such functionality, e.g., components such as a battery, display, and the one or more biometric sensors. Such a housing may also include components that provide other functionality, such as radio-frequency (RF) transmitters and receivers (including for communication, e.g., WiFi or Bluetooth, or for navigation, e.g., GPS, GLONASS, or other GNSS system). In a typical RF transmitter or receiver system, electrical signals are generated or received by transmitter or receiver. In the case of a transmitter, the transmitter generates alternating current that has a frequency in the RF spectrum (in the 3 kHz to 300 GHz range) which is then supplied to an antenna, which may also be referred to as an RF radiator. When the alternating current is applied to the RF radiator, it causes electromagnetic waves to be generated that radiate outwards from the RF radiator; these electromagnetic waves (often referred to as radio or RF waves or signals), may travel through space until they are intercepted by another RF radiator that converts the electromagnetic waves back into an alternating current that is fed to a receiver. RF radiators may be connected to both receivers and transmitters (sometimes referred to as a transceiver), and may both receive and transmit RF waves. Transmitters and receivers may be connected with their respective RF radiators by way of a feed line (also referred to herein as an RF feed), which is a cable or other electrically conductive pathway that is configured to transmit the alternating current signal between the RF radiator and the transmitter and/or receiver.

"RF radiator" or "RF radiator portion" is used herein to describe a structure that is engineered to act as an RF antenna. Such structures may be designed to produce an electromagnetic field that has a particular desired directionality and strength/field distribution. While all electronic components may emit some degree of electromagnetic radiation, it is to be understood that RF radiators are purpose-built (or designed) to convert electrical energy into RF signals intended to be received by a remote RF receiver and/or, conversely, to receive RF signals from a remote transmitter and convert those RF signals into electrical signals fed to an RF receiver. Components that emit RF radiation incidentally, instead of as their primary electrical purpose, are not considered to be "RF radiators" or "RF radiator portions" in the context of this application.

RF radiators are typically sized and designed to receive RF signals that are of a particular frequency. When such RF radiators come into contact with other structures or objects that change the electrical properties of such RF radiators, they may suffer a degraded ability to transmit or receive the RF signals that they are designed for. Accordingly, it is common practice in wearable devices to isolate any RF radiators that are used from contact with the external environment. Thus, for example, Fitbit activity trackers such as the Fitbit Zip, One, Flex 2, Alta, Alta HR, Charge, Charge HR, Charge 2, Blaze, and Surge have all included Bluetooth transceivers and, in the case of the Surge, a GPS receiver, but the RF radiators for those systems have been located entirely within their respective housings to prevent them from contacting external objects, e.g., skin, bracelets, etc., that might alter their RF performance. Similarly, the Apple Watch, Samsung Gear Fit, Basis B1, and Garmin Vivosmart wearable fitness trackers also utilize internally-located RF radiators. In many cases, these are simply conductive traces on a flexible printed circuit board located within the housing, or are conductive traces printed on a rigid printed circuit board.

It is to be understood that "wearable" devices, as the term is used herein, refers to articles that are worn by a user such that they are in contact with the person's skin; during both active use as well as non-active (passive) use, as opposed to portable devices that are grasped by a user during active use but not generally positioned against the user's skin during passive use. Watches, bracelets, necklaces, and armbands are examples of "wearable" devices, whereas hand-held cell phones, PDAs, and tablets are not considered "wearable" in the context of this application.

In some housings, similar to the ones discussed below, the housing itself may include one or more RF radiator portions that form part of the exterior of the housing. Thus, each such RF radiator portion may provide one or more external surfaces of the housing, i.e., be part of the overall external appearance of the housing, but may also provide RF antenna functionality at the same time.

To facilitate such implementations, the housing may be divided into discrete components that are connected together in some fashion. Such a housing may include, for example, at least a first RF radiator portion, a base portion, and an electrically non-conductive intermediate structure that is interposed between the base portion and the first RF radiator portion. The base portion and the first RF radiator portion may both be made of a non-ferrous metal, e.g., an aluminum alloy or magnesium alloy, (the same material may be used for both, or different materials may be used for each). The electrically non-conductive intermediate structure may be made from any of a variety of materials that are commonly considered electrically non-conductive or electrically insulating, e.g., plastic or glass. In some implementations, the base portion may be made of a non-ferrous metal, but may also have portions that are made of other materials, e.g., a rubberized coating or a layer of paint that may provide the exterior surfaces of the housing. In these instances, it is to be understood that the base portion may still be viewed as being made of a non-ferrous metal even if some small portion of it is made from such other materials.

In some such implementations, the first RF radiator portion may be completely electrically isolated from the base portion by the electrically non-conductive intermediate structure, i.e., an electrical continuity test between the first RF radiator portion and the base portion will fail, whereas in other implementations, the first RF radiator portion and the base portion may be in electrical contact with each other in one or more locations, but may predominantly be separated from each other by the electrically non-conductive intermediate structure.

The exterior of the housing, it will be understood, refers to the exterior surfaces of the housing that may be touched by an external object, e.g., a finger, a pencil tip, etc. when the device that the housing is part of is fully assembled. Surfaces of the housing that are not accessible to such contact when the device that the housing is part of is fully assembled may be thought of as interior surfaces. The exterior surfaces of the housing may, for example, include a back surface that is in contact with a person's skin when the apparatus having the housing is worn by the person. The back surface may be provided by the base portion or may include surfaces provided by components mounted to the base portion. For example, if the base portion includes a transparent window element, as may be used to allow optical components such as photoemitters and photodetectors within the housing to transmit and receive light to and from a wearer's skin, the exterior surface provided by the transparent window element may provide part of the back surface in addition to the surfaces of the base portion adjacent to the transparent window element.

In contrast to the back surface provided by the base portion, the first RF radiator portion may be positioned within the housing such that the exterior surfaces of the housing included in the first RF radiator portion generally face away from the wearer's skin that contacts the back surface of the housing when the wearable electronic device is worn by the wearer. As will be understood with reference to the later-discussed Figures below, the first RF radiator portion may include multiple exterior surfaces, with a major exterior surface or surfaces, i.e., more than 50% of the exterior surfaces or surfaces included in the first RF radiator portion, that face away from the wearer's skin. There may also be some exterior surfaces of the first RF radiator portion that face towards the wearer's skin, but these surfaces may form only a small fraction, e.g., less than 5%, 10%, 15%, 20%, or 25%, of the exterior surfaces provided by the first RF radiator portion. Thus, the exterior surfaces of the housing provided by the first RF radiator portion may be viewed as "generally" facing away from the wearer's skin that contacts the back surface of the housing when the wearable electronic device is worn by the wearer. Such a configuration reduces the risk that the first RF radiator portion will come into contact with the wearer's skin, thereby reducing the chance that the RF characteristics of the first RF radiator portion may be negatively impacted by such contact. At the same time, the fact that the first RF radiator portion in integrated as part of the housing provides an elegant RF antenna solution that eliminates the need to provide for room inside of the housing for an antenna. In the context of a wearable device in which packaging volume is at a premium, this allows the volume that would ordinarily be used to accommodate an antenna to be used for other purposes, such as increased battery volume (and thus increased battery capacity).

As noted earlier, the housing may contain various components, including, for example, a first RF receiver (or transmitter or transceiver; a receiver, as the term is used herein, may refer to a device that is only a receiver or to the portion of a transceiver that provides receiver functionality). The first RF receiver may, for example, be a GPS receiver configured to receive GPS RF signals in the 1575.42 MHz and 1227.6 MHz ranges (e.g., in the 1100 to 1700 MHz range), or may be a WiFi or Bluetooth receiver configured to receive RF signals in the 2.4 GHz to 2.5 GHz range (or, more generally, in the 2.2 to 2.7 GHz range), or may be a cellular (e.g. GSM, GPRS, EGPRS, CDMA, WCDMA, LTE) receiver configured to receive RF signals in 600 MHz to 4 GHz range. In some implementations, the first RF receiver may include a plurality of receivers (or transceivers) that may be connected with the first RF feed using a diplexer or multiplexer, thereby allowing a single RF feed to be switched between multiple receiver types. For example, the first RF feed may be connected to a diplexer or multiplexer that may be used to switch between a GPS receiver, a Bluetooth transceiver, a cellular transceiver, and/or a WiFi transceiver. In some such implementations, the multiplexer or diplexer may be configured to not only switch between different receivers or transceivers, but may also be configured to switch between different RF feeds, e.g., between a first RF feed and a second RF feed similar to the first and second RF feeds discussed below. In some such implementations, the feeds that are switched between may be located on the same radiator portion, but at different locations. For example, a diplexer may switch between first and second RF feed locations that are located on the same RF radiator portion (such as would be achieved by aligning and overlaying, for example, the first RF radiator portion discussed below with the second RF radiator portion discussed below, and then providing a second RF feed on the first RF radiator portion in the same location as the second RF feed on the second RF radiator portion). This may allow a single RF radiator portion to provide RF functionality for two or more RF components that operate in different frequency bands while still providing acceptable RF performance for each RF component. The first RF receiver may be electrically connected with a first RF feed that may be placed into electrically conductive contact with the first RF radiator portion in order to conduct the RF-frequency current generated by the first RF radiator portion in response to detecting an RF signal to the first RF receiver. In the event that the first RF receiver is part of a transceiver or, alternatively, replaced with a transmitter, the same first RF feed may be used to convey an RF-frequency alternating current to the first RF radiator portion from the transceiver or transmitter.

Generally speaking, the various portions that are included in the housing may be connected with the electrically non-conductive intermediate structure to form a single, unitary component. For example, in some implementations, the electrically non-conductive intermediate structure may be connected with the first RF radiator portion and the base portion through an adhesive layer that bonds them together. In some other implementations, the first RF radiator portion, the base portion, and the electrically non-conductive intermediate structure may be formed as a nano-molded assembly. Nano-molding is a technique for making unitary, plastic-metal hybrid parts in which metal components, such as the base portion and the first RF radiator portion, are treated so as to cause surfaces of those components that will be in contact with the plastic to be roughened, thus generating microscopic pits and fissures in those surfaces. Such surfaces may also include positive- or negative-relief features, e.g., grooves, ridges, etc., that are macroscopic in nature. Subsequent to such surface roughening, the metal components may be placed into an injection molding die and positioned relative to each other and the die and molten plastic, such as a glass-fiber filled plastic, may be injected into the die. The molten plastic will flow into the gaps between the metal parts and into the microscopic pits and fissures, resulting in a strong mechanical bond between the plastic component and the adjacent metal components. The resulting structure will be a single, unitary component in which the electrically non-conductive intermediate structure, made of plastic, joins the first RF radiator portion and the base portion together.

It is to be understood that additional RF radiator portions may be included in such a housing; these additional RF radiator portions may have similar characteristics to those discussed above with respect to the first RF radiator portion, although they may differ slightly in some respects, as discussed in more detail below. In some implementations, there may be two externally symmetric RF radiator portions positioned on opposing sides of another component, e.g., a display unit. In some such implementations, these RF radiator portions may be generally trapezoidal in shape so that they transition from the width of the display unit to a narrower width, e.g., such as the width of straps that may be attached to the housing (they may vary slightly from these widths, e.g., be within ±5% of these widths, in some implementations). In some such implementations, the trapezoidal shape may be between 3 and 7 times longer along the long axis (which may be parallel to the parallel portions of the trapezoid) as compared with its width.

Figure 21:
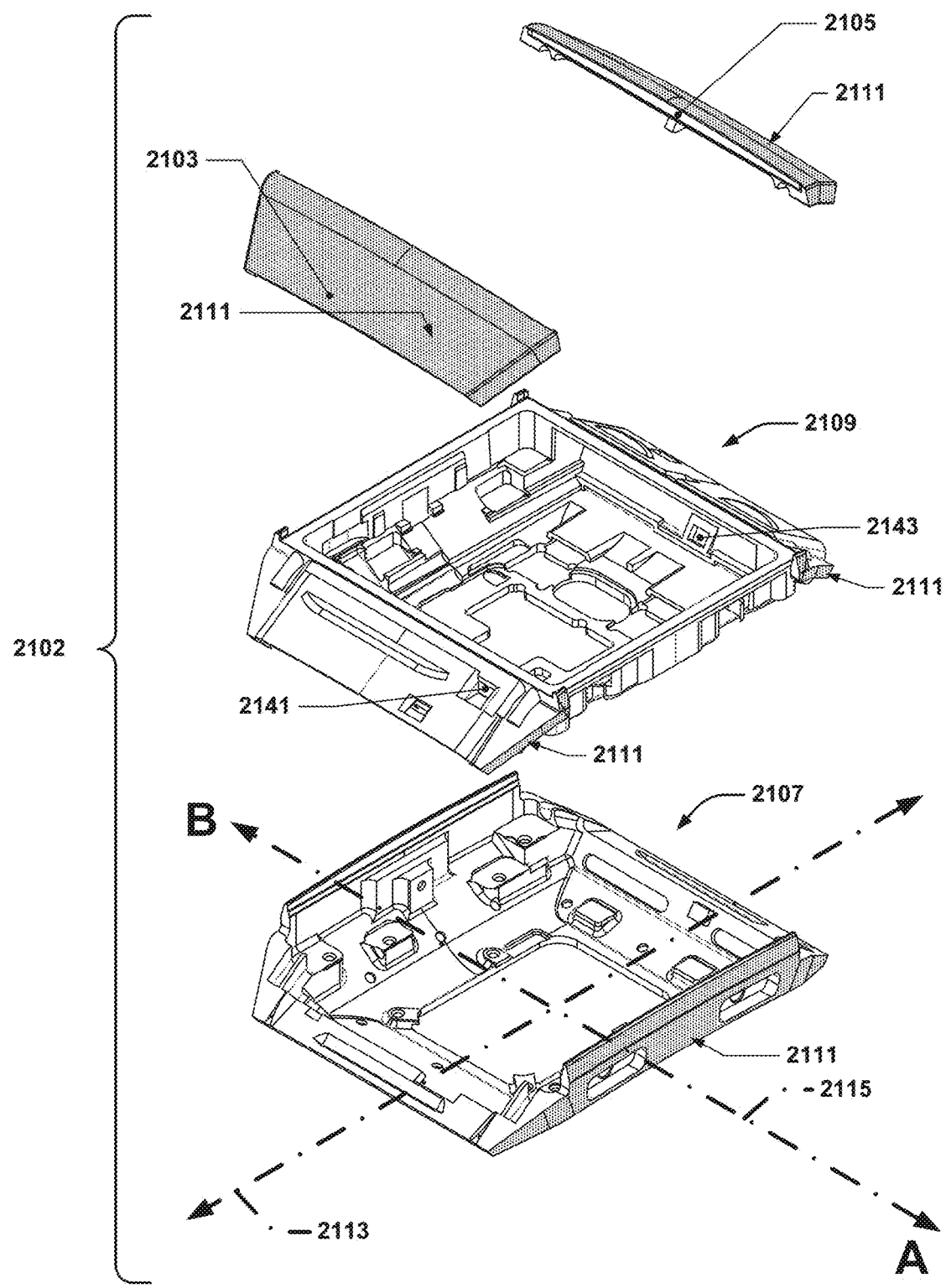
FIG. 21 depicts an isometric exploded view of an example housing for a biometric monitoring device.

FIG. 21 depicts an isometric exploded view of an example housing for a biometric monitoring device. Although not shown in this Figure, the housing may be connected with straps, bands, or other accessories in order to be worn on a person's wrist or forearm. It will also be appreciated that such accessories may be removable, as discussed earlier herein, or may be permanently connected with the housing, e.g., glued, bonded, co-molded, or otherwise permanently connected. As can be seen in FIG. 21, housing 2102 includes a base portion 2107, a first RF radiator portion 2103, and a second RF radiator portion 2105, all of which may be made of a non-ferrous metal, such as aluminum. These components may also be anodized or otherwise coated with a protective and/or decorative coating. Also visible in FIG. 21 is an electrically non-conductive intermediate structure 2109, which may have a first RF feed-through 2141 and a second RF feed-through 2143 (e.g. openings in the non-conductive intermediate structure 2109), as well as reference axes, such as centerline 2113 and transverse axis 2115. The transverse axis 2115 may be understood to be an axis that is generally aligned with a wearer's forearm when the device incorporating the housing is worn by the wearer. In this example, the end of the transverse axis 2115 that points towards "A" may be understood to be pointed towards the wearer's left hand when worn on the wearer's left wrist, with the end pointing towards "B" oriented towards the wearer's left elbow. While the housing may also be worn on a wearer's right wrist, with resulting transpositions of the A and B directions, the left-wrist frame of reference may have particular relevance, as more than 75% of a sample population who wear such devices have been observed to wear them on their left wrists. Exterior surfaces 2111 of the housing are also shown (such exterior surfaces have been shaded in grey to facilitate their identification).

Figure 22:
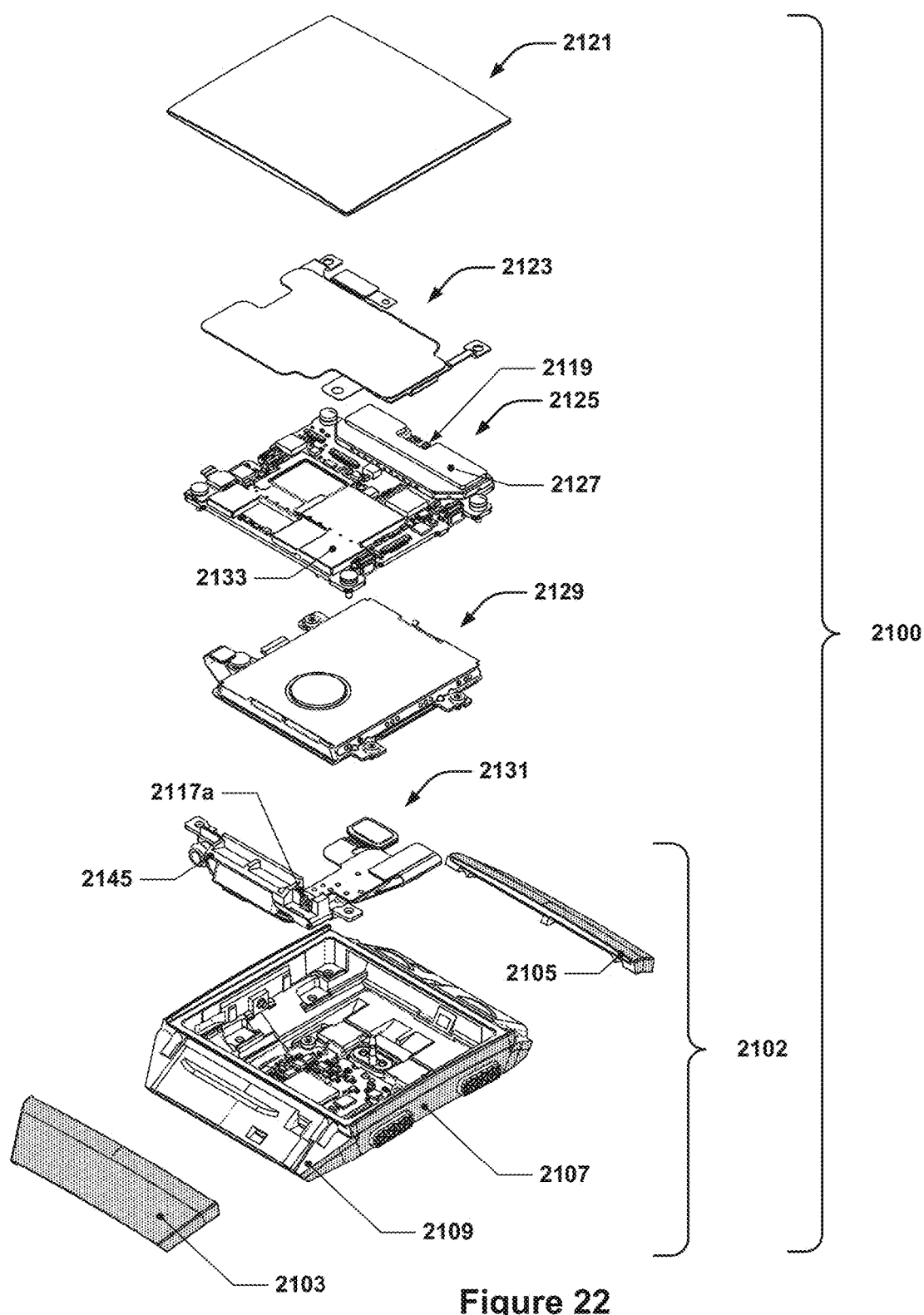
FIG. 22 depicts an isometric exploded view of an example biometric tracking device using a housing such as that shown in FIG. 21.
Figure 23:
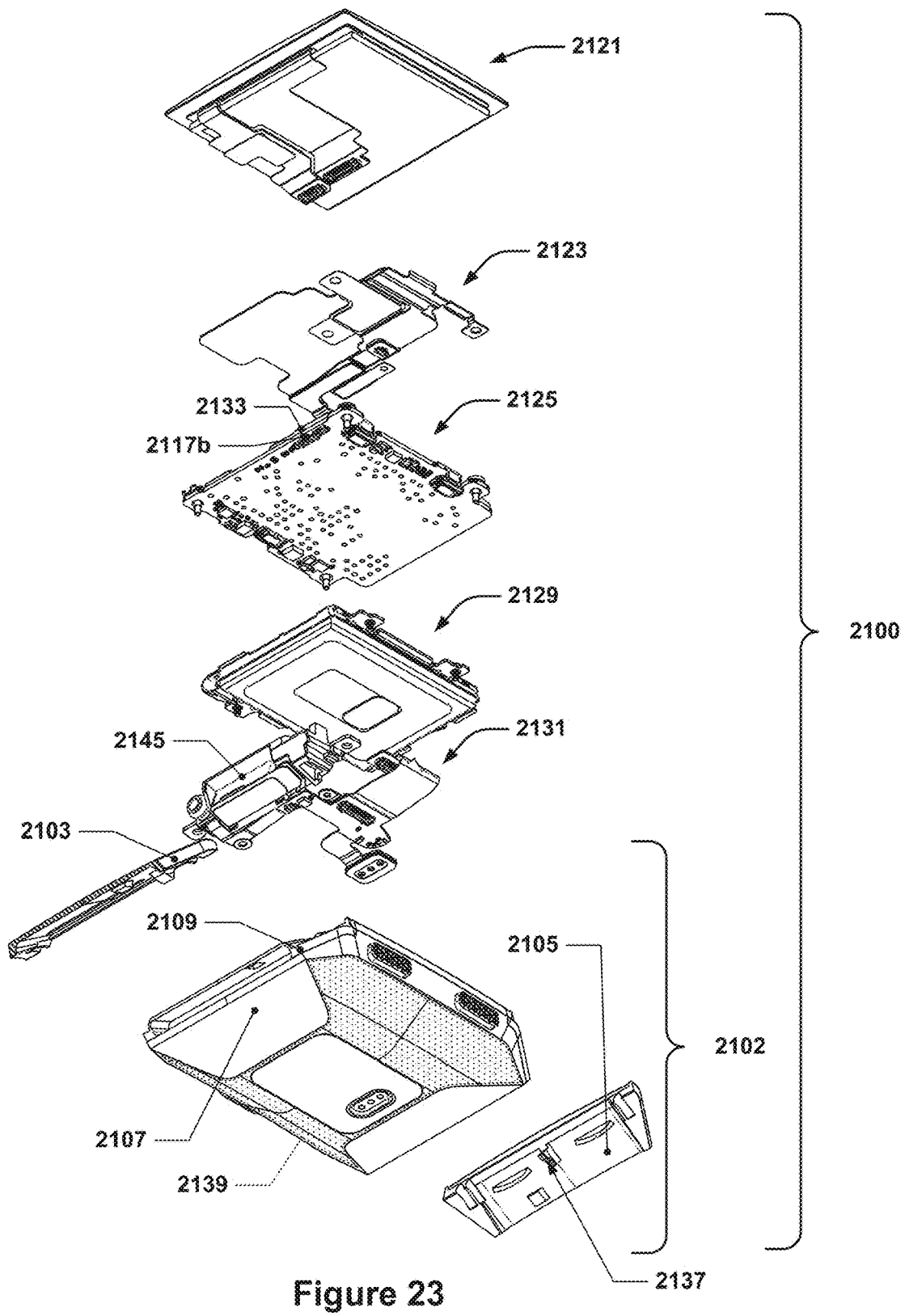
FIGS. 23 and 24 are isometric exploded views of the example biometric monitoring device of FIG. 22 from different perspectives.
Figure 24:
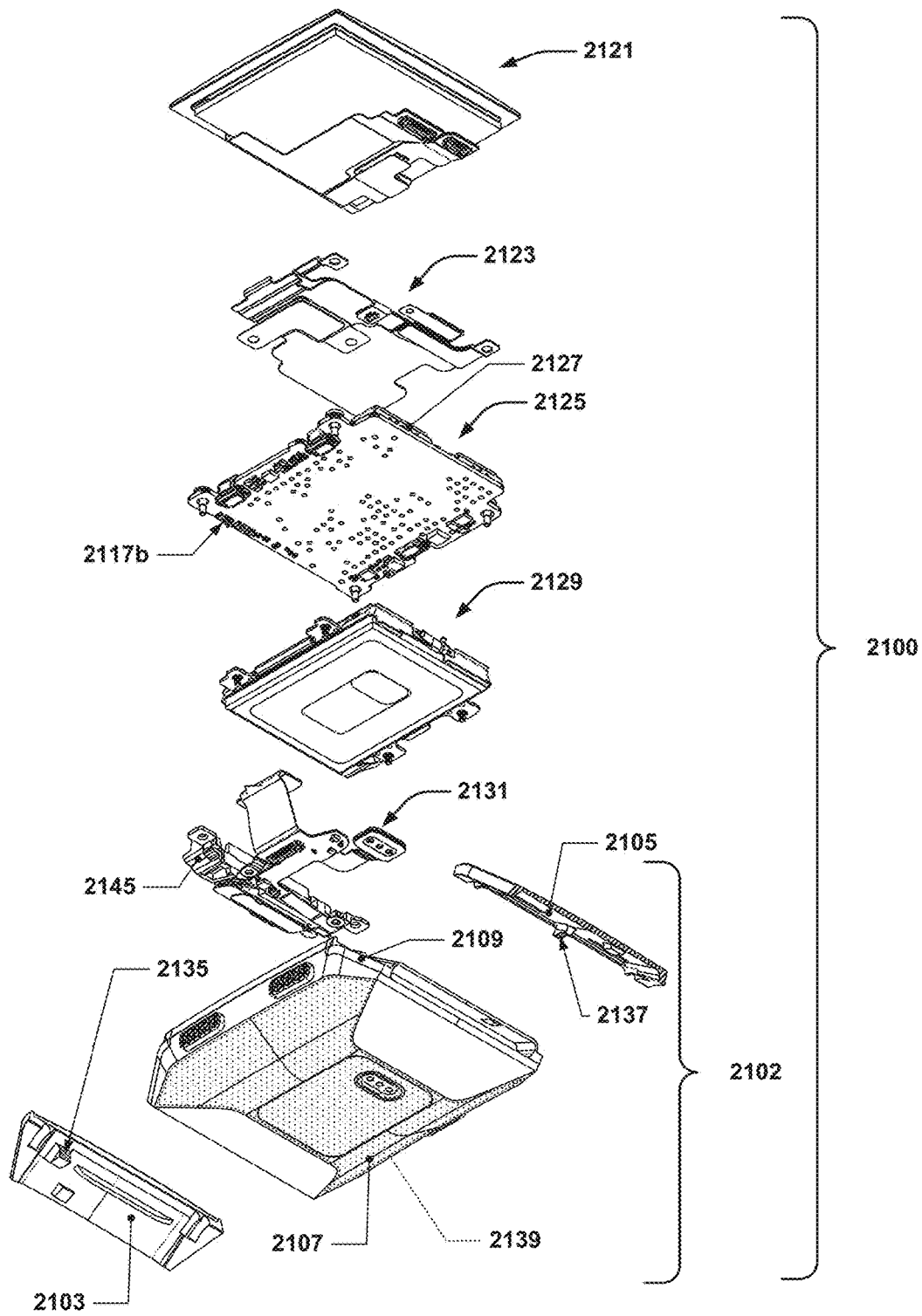

FIG. 22 depicts an isometric exploded view of an example biometric tracking device using a housing such as that shown in FIG. 21. FIGS. 23 and 24 are isometric exploded views of the example biometric monitoring device of FIG. 22 from different perspectives.

As is evident in FIGS. 22 through 24, the packaging within a wearable electronic device, such as fitness tracker 2100, may be quite dense or tight, with multiple levels of components arranged in a highly-integrated package. In FIG. 22, for example, the housing 2102 is shown partially exploded—with the first RF radiator portion 2103 and the second RF radiator portion 2105 shown as removed from the base portion 2107 and the electrically non-conductive intermediate structure 2109. Mounted within the housing 2102 is a sensor circuit board (unlabeled, but visible). An auxiliary printed circuit board (PCB) 2131 may be supported within the housing 2102 by a bracket 2145, for example, which may include a portion of a first RF feed 2117, e.g., portion 2117a; this portion 2117a of the first RF feed 2117 may, when the auxiliary PCB 2131 and the bracket 2145 is installed into the housing 2102, protrude into or through the first RF feed-through 2141, where it may establish electrically conductive contact with the first RF radiator portion 2103. A battery 2129 may be layered on top of portions of the auxiliary PCB 2131, followed by a main PCB 2125, which may include components such as a first RF receiver 2133 and a second RF receiver 2127, as well as a second RF feed 2119, which may, when the main PCB 2125 is inserted into the housing 2102, make electrically conductive contact with the second RF radiator portion 2105 through the second RF feed-through 2143. In some implementations, a near-field communications (NFC) antenna 2123 may be included as well. A display unit 2121 may seal off the internal components from the ambient environment, and may provide a further exterior surface of the device.

As can be seen in FIGS. 23 and 24, the main PCB 2125 may also include another portion of the first RF feed 2117b that may contact the first RF feed 2117a (or a conductive trace leading thereto) and provide an electrically conductive pathway between the first RF receiver 2133 and the first RF radiator portion 2103.

Generally speaking, the electrically non-conductive intermediate structure may act to separate the RF radiator portion(s) and the base portion by approximately 1 mm or more, e.g., ~1.2 mm or between 0.8 mm and 1.5 mm; this provides adequate separation to provide good RF performance by the RF radiator portion(s). Furthermore, while it is often considered desirable from an RF perspective to use plastic components to avoid or reduce interference to the RF signals received by the antennas, it was discovered during development of the concepts herein that a predominantly metal housing actually provided better performance than a plastic or predominantly plastic housing. This is believed to occur because the metal base portion shields the RF components from interference or loading from the human body, which is in close proximity.

For example, in simulations performed under various conditions for a baseline design in which the metal of the base portion only existed in the shaded regions of the base portion 2107 shown in FIG. 23 (rather than extending across the entire base portion), with the remainder of the base portion being replaced with the material of the electrically non-conductive intermediate structure, the first RF radiator portion exhibited a radiation efficiency of −2.0 dB in free space and −8.4 dB when worn on a person's wrist. Somewhat surprisingly, in similar simulations performed with the base portion shown in FIG. 21, while the first RF radiator portion had a radiation efficiency of −2.3 dB in free space (worse than the baseline design), the radiation efficiency when worn on the wrist was superior at −7.7 dB. Thus, there was an unexpected benefit to making the base portion out of metal.

In the example device of FIGS. 22 through 24, the first RF radiator portion 2103 may have a first RF feed contact point 2135 (see FIG. 23), and the second RF radiator portion 2105 may have a second RF feed contact point 2137 (see FIGS. 23 and 24). These RF feed contact points 2135 and 2137 may be left unanodized or otherwise uncoated by any protective and/or decorative coating that might interfere with electrical conductivity to ensure good electrically conductive contact. As can be seen in FIGS. 24 and 23, some exterior surfaces (indicated with diagonal cross-hatching) of the first and second radiator portions may be oriented towards the wearer's skin when the fitness tracker 2100 is worn, but the majority of the exterior surfaces of the first and second radiator portions are oriented away from the wearer's skin when the fitness tracker 2100 is worn.

Figure 25:
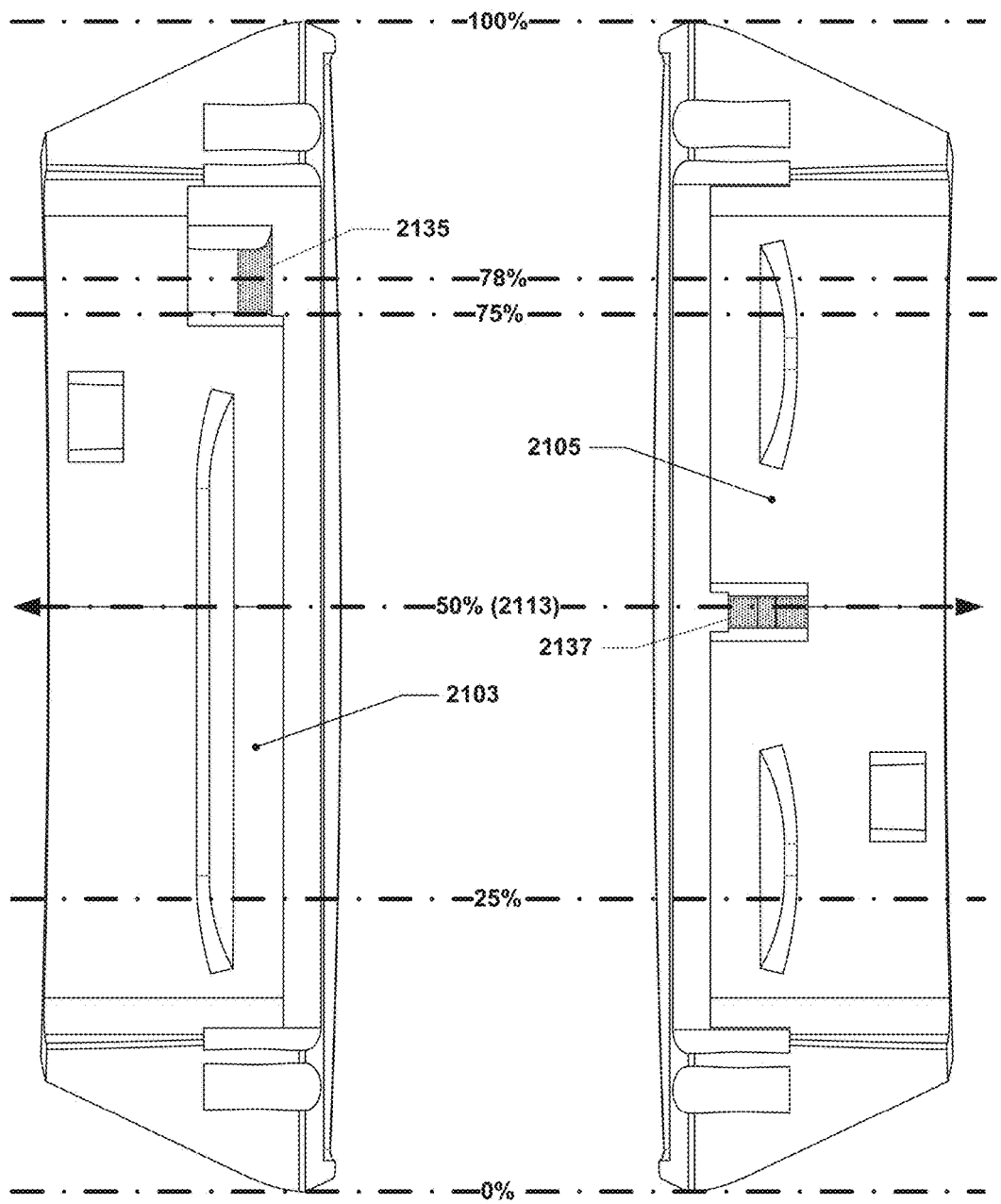
FIG. 25 depicts plan views of the example RF radiator portions of the example housing in FIG. 22.

FIG. 25 depicts plan views of the example RF radiator portions of FIGS. 26 and 27. FIG. 26 depicts a further cross-sectional view of the example biometric monitoring device of FIG. 22 taken through a sectioning plane offset from a mid-plane of the housing (such a plane would be at approximately the 78% mark shown in FIG. 25). FIG. 27 depicts a cross-sectional view of the example biometric monitoring device of FIG. 22 taken through the mid-plane of the housing.

In FIG. 26, it can be seen that the first RF feed 2117 (specifically, portion 2117a) contacts the first RF radiator portion at the first RF feed contact point 2135. It can also be seen that portions 2117a and 2117b contact each other, thereby providing an electrically conductive path. Due to the fact that the first RF feed contact point 2135 is somewhat recessed inside of the housing 2102, the first RF feed 2117 or, in this case, the portion 2117a of the first RF feed 2117, may take the form of a sprung electrical contact, e.g., a leaf spring, that is compressed against the first RF feed contact point 2135 when the internal component, e.g., the bracket 2145 with the auxiliary PCB 2131 attached in this case, having the first RF feed is installed in the housing 2102. As can be seen from FIG. 25, the first RF feed contact point 2135 is located at an offset location with respect to the centerline 2113 of the housing 2102. Such an offset location causes the radiation pattern of the first RF radiator portion 2103 to be asymmetric with respect to at least the centerline 2113, with an increased sensitivity/gain to signals approaching the first RF radiator portion 2103 from the side of the first RF radiator portion 2103 that is furthest from the first RF feed contact point 2135 (in FIG. 25, this would correspond to signals approaching the first RF radiator portion 2103 from the bottom of the page relative to the page orientation).

A first RF radiator portion 2103 with a first RF feed contact point 2135 that is offset from the centerline of the housing, as shown in FIG. 25, may be particularly well-suited for receiving GPS, GLONASS, or other GNSS geolocation signals in certain contexts, including, for example, in many wrist-wearable devices.

As a first matter, GPS and GLONASS (a Russian system similar to GPS) utilize lower-frequency carrier signals, e.g., 1575.42 MHz and 1227.60 MHz for GPS or a 1602 MHz or 1246 MHz center frequency with n*0.4375 MHz offsets for n frequency channels for GLONASS. Such frequencies may have wavelengths in the 7.4 to 9.6 inch range. For lower-frequency antennas used in wearable devices, it may be desirable to provide an RF radiator structure that attempts to maximize (to the extent practically possible considering competing factors, such as packaging space, assembly tolerances, manufacturing limitations, and other factors) the distance between the feed location or feed contact point for the antenna and the furthest portion of the antenna from that location. This is because it is generally desirable to have an antenna be of approximately the same length as the wavelength of the signals that it is designed to receive or transmit, or some ½ multiple of that length, e.g., a half-wave, quarter-wave, or eighth-wave antenna. In the case of GPS signals, it may not be practical in the context of a radiator portion for a wearable device to implement a single-wavelength antenna length, but a ⅛$^{th}$ wave antenna may be possible. Accordingly, it may be desirable to implement an RF radiator portion for use with GPS or GLONASS signals such that the RF feed contact point for that RF radiator portion is located (or centered) in the outer 25% region (measured along the transverse axis) of the RF radiator portion; the remaining >75% portion of the RF radiator portion may thus act as the antenna and, in a typical wearable device (one, for example, in which the housing is less than 2 inches, 1.75 inches, or 1.5 inches across), provide good performance at the GPS or GLONASS frequency bands.

In addition to using an off-center placement of the RF feed or RF feed contact point, the first RF radiator portion and the first RF feed and/or RF feed contact point may, in scenarios where such components are used for GPS or GLONASS signals, be located in particular positions that may be particularly well-suited to the context of wearable devices. In comparison to other types of RF signals, geolocation RF signals are somewhat predictable with regard to their source locations—such signals originate from satellites in high orbit, and therefore tend to approach a receiving antenna from a location above the receiving antenna. In the context of a wearable device, such as a watch or other wrist-worn system, it may be advantageous to locate the first RF radiator portion first RF feed contact point 2135 and/or first RF feed 2117, e.g., the portions 2117a and 2117b, such that it is more likely to receive such signals with a higher gain, thereby improving the performance of the geolocation system.

Figure 28:
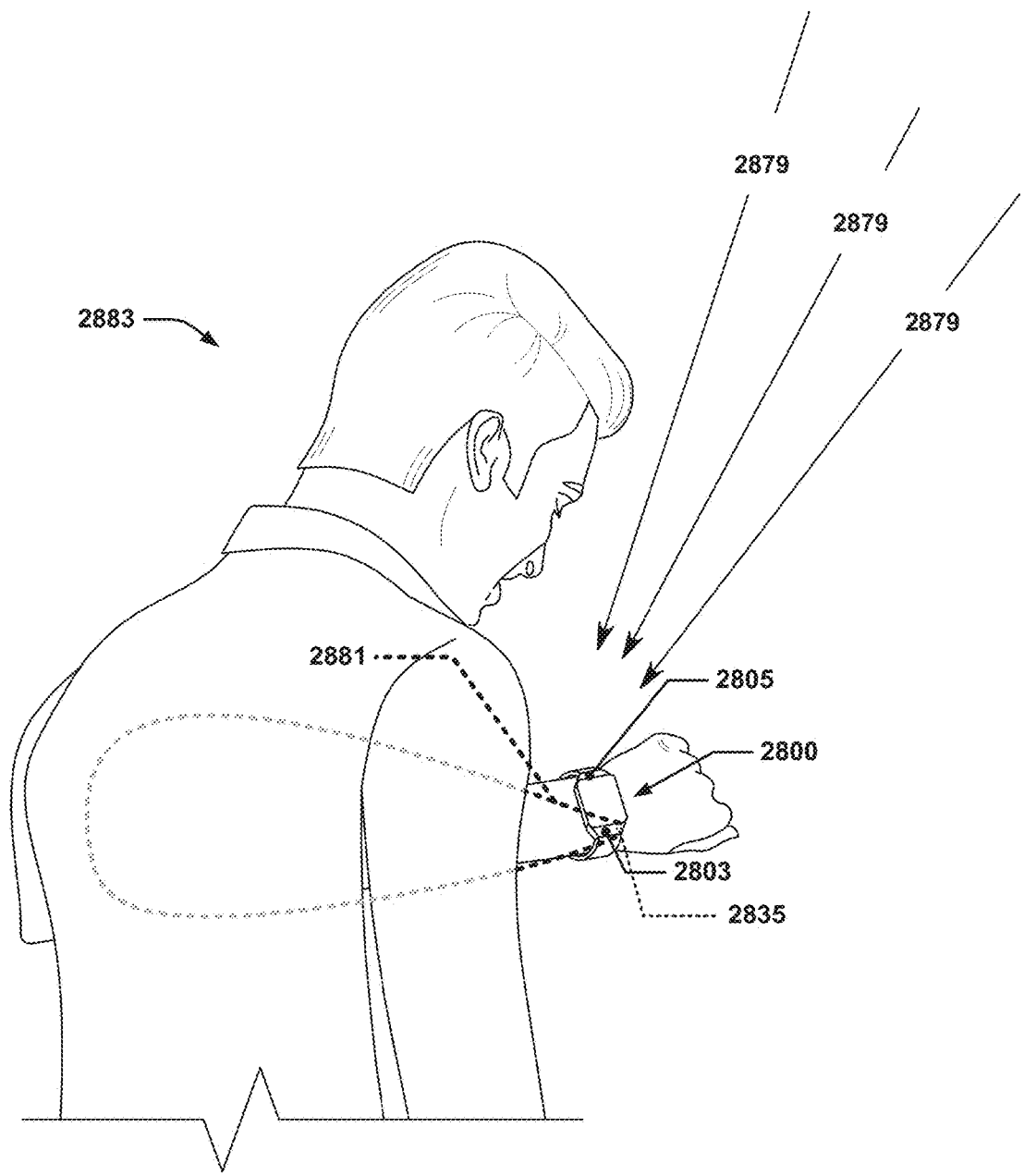
FIG. 28 depicts a diagram showing a particular orientation of a wearable device and various RF-related features associated therewith.
Figure 29:
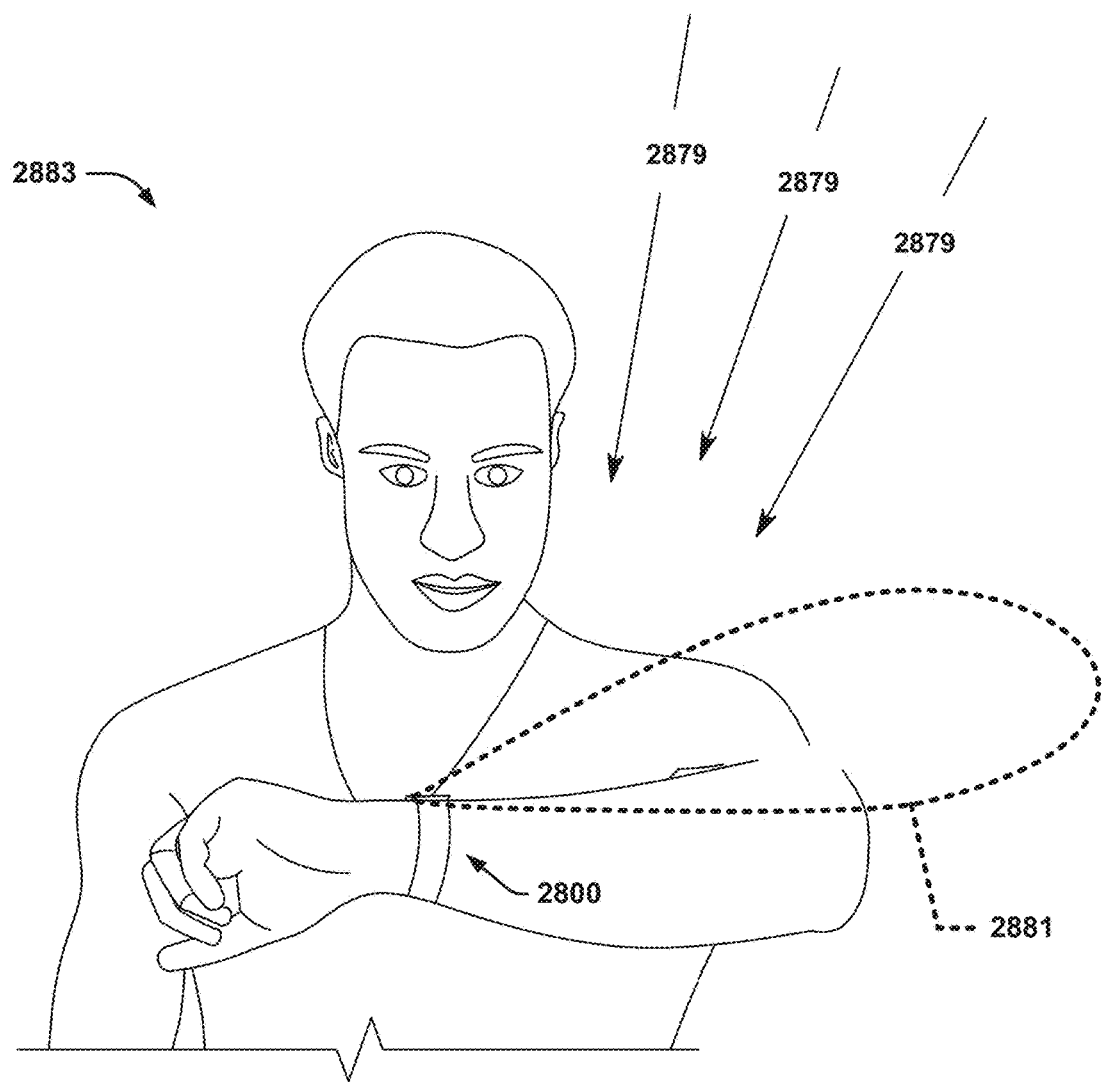
FIG. 29 depicts a diagram showing another orientation of a wearable device and various RF-related features associated therewith.

For example, it may be desirable to locate the first RF radiator portion such that it is located near the "bottom" of the housing when the housing is oriented such as it would be when worn on a person's wrist (see FIG. 28) and held in front of the person with the display of the device oriented towards the person's face, such as may be done when reading the time. In FIG. 28, a person 2883 is wearing a fitness tracker 2800 that has a first RF radiator portion 2803 and a second RF radiator portion 2805. The first RF radiator portion 2803 has a first RF feed contact point 2835 that is positioned similarly with respect to the first RF radiator portion 2803 as the first RF feed contact point 2135 is positioned with respect to the first RF radiator portion 2103. The radiation pattern 2881 that such an antenna structure has generally extends away from the first RF radiator portion 2803 towards the person's elbow (when person is wearing the fitness tracker on, in this case, their left hand) the and in a direction generally aligned with the person's forearm. In FIG. 28, the person 2883 is holding their left arm generally horizontal and in front of them, causing the radiation pattern 2881 to be less effective, thereby making the system somewhat less effective at receiving radio signals, e.g., GPS signals, 2879. FIG. 29 shows the same general orientation of the person's arm and the fitness tracker, but from a front perspective. This orientation assumes that the housing is worn against the outer or upper surface of the wrist/forearm (opposite the palm).

While such a position may cause the first RF radiator portion 2103 to be partially occluded (with respect to GPS signals) by the rest of the housing when the device is oriented in this fashion, this orientation is typically only a transient one, e.g., it only occurs when the person is looking at the device. During "passive" use, e.g., when the device is merely being worn and not actively used, the first RF radiator portion 2103 located at the "bottom" of the housing may generally be oriented upwards or outwards (from the wearer's body), thereby reducing the chance of occlusion by the rest of the housing.

Figure 30:
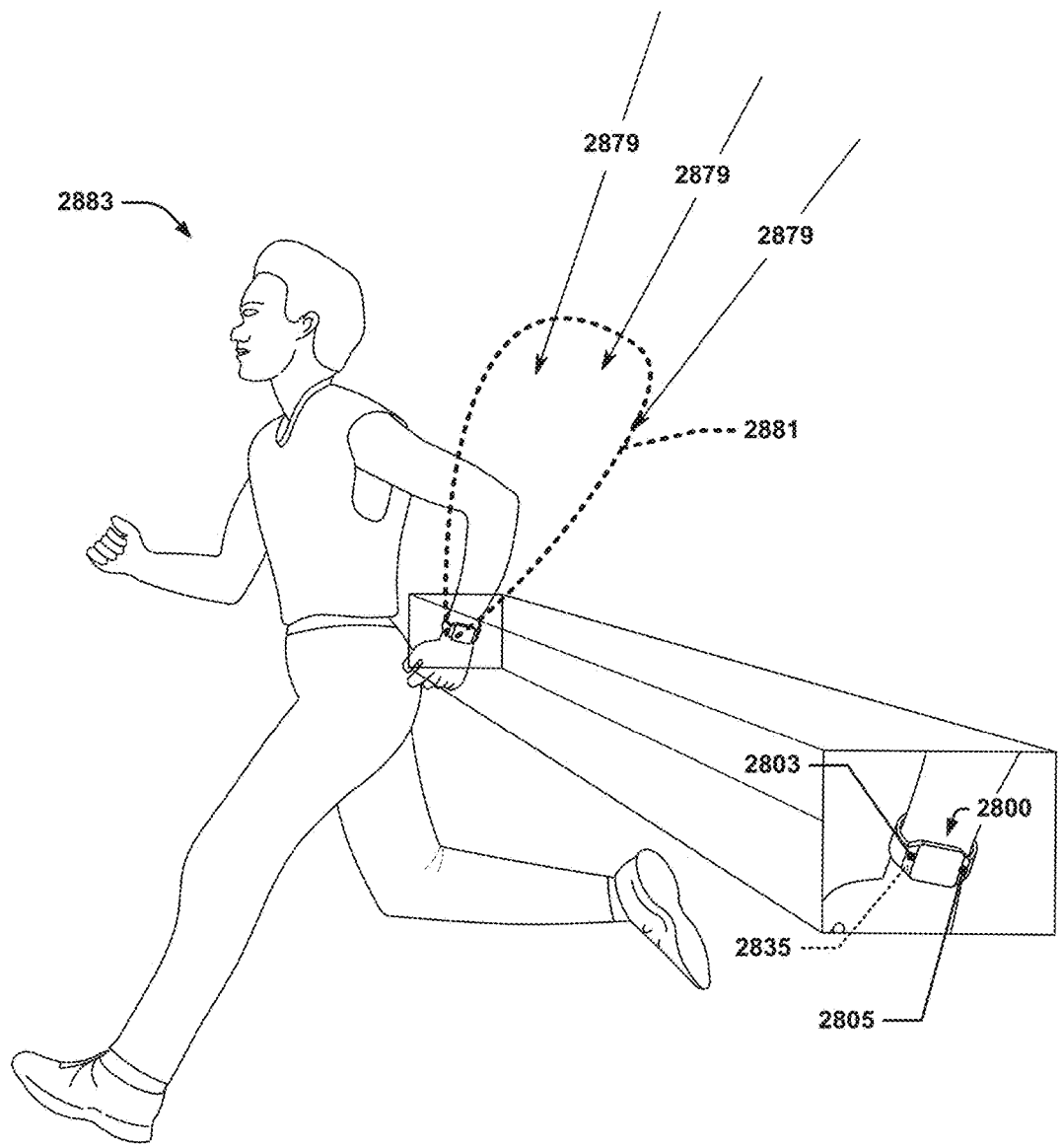
FIG. 30 depicts a diagram showing another orientation of a RF-related wearable device and various features associated therewith.

Furthermore, it may also be desirable to position the first RF feed and/or first RF feed contact point so that it is located closer to the wearer's hand when the wearable device is worn on the person's wrist. This may cause the resulting antenna gain of the first RF radiator portion to be at a maximum in a direction generally oriented towards the person's elbow (when the device is worn). Thus, when the person's arm is hanging at their side, the radiation pattern will generally be oriented with the peak gain pointed towards the sky, where it may be more sensitive to GPS signals transmitted by orbiting satellites. Similarly, when the person is running or walking and swinging their arms, the radiation pattern may continue to be generally oriented skywards (although oscillating between diagonally upwards (as shown in FIG. 30) and diagonally downwards depending on how the person's arms move when running). In FIG. 30, the person 2883 is running, and their left arm with the fitness tracker 2800 may oscillate as described above. As can be seen, the radiation pattern 2881 may, during such motion, point more towards the radio signals 2879, thereby exhibiting greater receptivity to such signals in such orientations.

It will become readily apparent that the orientation of the radiation pattern will be reversed if the wearable device is switched from one hand to the other (without rotating the wearable device). Accordingly, some implementations may be configured such that the above radiation pattern orientation pattern occurs when the wearable device is worn on the wearer's left wrist, as this is the predominant wrist that is used for such purposes in the general population. Other implementations, however, may be configured for right-handed wear, and may have the requisite first RF feed and first RF feed contact point located on the opposite side of the first RF radiator portion.

In some implementations, there may be a set of switchable RF feeds that are positioned on opposite sides of the first RF radiator portion 2103. In such implementations, the wearable device may include functionality that allows the wearer to specify on which wrist the wearable device is being worn, and a processor of the wearable device may cause the RF feed furthest from the wearer's wrist to deactivate, thereby allowing the radiation pattern to be moved from one side of the wearable device to the other.

In FIG. 27, it can be seen that the second RF feed 2119 contacts the second RF radiator portion 2105 at the second RF feed contact point 2137. In this depicted implementation, the second RF feed contact point 2137 is located approximately (e.g., within ±5% of the width of the housing perpendicular to the centerline) along the centerline 2113 of the housing 2102 (see FIG. 25). As a result, the second RF radiator portion 2105 may act, in effect, as two generally identical and opposite-facing radiators (each extending away from the second RF feed contact point 2137 in opposing directions) and may thus have a generally symmetric radiation pattern with respect to the left/right sides of the centerline 2113. Such a radiation pattern may be well-suited for receiving and transmitting RF signals that do not have a predictable source direction or vector. In particular, such a radiation pattern may be well suited for receiving WiFi or Bluetooth signals, which may have wavelengths of approximately 5 inches (a 2.4 GHz signal has a wavelength of 4.918 inches, for example). In a housing that has a width of approximately 1.5 inches, this may allow for each "radiator" to be approximately 0.75 inches in length. Since Bluetooth or Wifi signals may be received from nearly any direction (depending on the relative orientations of the receiver and the transmitter), a more balanced radiation pattern such as is provided by a centrally-located second RF feed contact point may be preferable for such implementations.

It is to be understood that the above disclosure, while focusing on a particular example implementation or implementations, is not limited to only the discussed example, but may also apply to similar variants and mechanisms as well, and such similar variants and mechanisms are also considered to be within the scope of this disclosure.

What is claimed is:

1. An apparatus comprising:
  a first radio-frequency (RF) receiver having a first RF feed; and
  a housing configured to be part of a wrist-wearable electronic device, wherein:
    the first RF receiver and the first RF feed are located within the housing,
    the housing has a plurality of exterior surfaces,
    the housing includes a base portion, a first RF radiator portion, and an electrically non-conductive intermediate structure that is interposed between, and connected with, the base portion and the first RF radiator portion,
    the base portion includes a back surface that faces a wearer's skin that contacts the wrist-wearable electronic device when the wrist-wearable electronic device is worn by the wearer,
    the base portion and the first RF radiator portion are made of metal,
    the first RF radiator portion includes one or more of the exterior surfaces of the housing,
    the first RF radiator portion is positioned within the housing such that the exterior surfaces of the housing included in the first RF radiator portion generally face away from the back surface,
    the first RF radiator portion is in electrically conductive contact with the first RF feed within the housing,
    the housing has a transverse axis that is substantially aligned with the wearer's forearm when the apparatus is worn on the wearer's forearm, and
    the first RF radiator portion has a first dimension along the transverse axis that is between 3 and 7 times longer than the longest dimension of the first RF radiator portion along an axis perpendicular to the transverse axis.

2. The apparatus of claim 1, wherein the electrically non-conductive intermediate structure maintains a separation distance of between 0.8 and 1.5 mm between the first RF radiator portion and the base portion.

3. The apparatus of claim 1, wherein the first RF radiator portion is electrically isolated from the base portion by the electrically non-conductive intermediate structure.

4. The apparatus of claim 1, wherein the base portion and the first RF radiator portion are made of a non-ferrous metal.

5. The apparatus of claim 1, wherein the base portion, the first RF radiator portion, and the electrically non-conductive intermediate structure are a nano-molded structure, with the first RF radiator portion and the base portion each having a plurality of microscopic fissures or pores arising from the nano-molding manufacturing process and the electrically non-conductive intermediate structure having portions extending into the microscopic fissures or pores.

6. The apparatus of claim 1, wherein the base portion and the first RF radiator portion are bonded to the electrically non-conductive intermediate structure with an adhesive layer.

7. The apparatus of claim 1, further comprising a second RF receiver having a second RF feed, wherein:
  the second RF receiver and the second RF feed are located within the housing,
  the housing further includes a second RF radiator portion,
  the electrically non-conductive intermediate structure is further interposed between, and connected with, the base portion and the second RF radiator portion,
  the second RF radiator portion is made of metal,
  the second RF radiator portion includes one or more further exterior surfaces of the housing,
  the second RF radiator portion is positioned within the housing such that the further exterior surfaces of the housing included in the second RF radiator portion generally face away from the back surface,
  the second RF radiator portion is in electrically conductive contact with the second RF feed within the housing, the electrically non-conductive intermediate structure maintains a separation distance of between 0.8 and 1.5 mm between the second RF radiator portion and the base portion, and the second RF radiator portion is electrically isolated from the base portion and the first RF radiator portion by the electrically non-conductive intermediate structure.

8. The apparatus of claim 7, wherein:
the first RF receiver is configured to operate in one or more first frequency bands that are in the 600 MHz to 2200 MHz range, and
the second RF receiver is configured to operate in one or more second frequency bands that are in the 1.5 GHz to 2.7 GHz range.

9. The apparatus of claim 1, further comprising:
a display unit, wherein the display unit is mounted in the housing such that a display surface of the display unit generally faces away from the back surface, and
the first RF radiator portion is positioned next to the display unit.

10. The apparatus of claim 1, wherein
the apparatus further comprises at least one wrist strap that is connected to the housing.

11. The apparatus of claim 10, wherein:
the housing has a centerline that is perpendicular to the transverse axis and nominally parallel to the back surface, and
the first RF feed makes electrically conductive contact with the first RF radiator portion in a location located on a side of the centerline closer to the wearer's left hand when the apparatus is worn by the wearer on the wearer's left forearm.

12. The apparatus of claim 11, wherein:
the location where the first RF feed makes electrically conductive contact with the first RF radiator portion is in a region of the first RF radiator portion that is within an outermost 25% of the first RF radiator portion that is closest to the wearer's left hand when the apparatus is worn by the wearer on the wearer's left forearm.

13. The apparatus of claim 12, further comprising a second RF receiver having a second RF feed, wherein:
the second RF receiver and the second RF feed are located within the housing,
the housing further includes a second RF radiator portion,
the electrically non-conductive intermediate structure is further interposed between, and connected with, the base portion and the second RF radiator portion,
the second RF radiator portion is made of metal,
the second RF radiator portion includes one or more further exterior surfaces of the housing,
the second RF radiator portion is positioned within the housing such that the further exterior surfaces of the housing included in the second RF radiator portion generally face away from the back surface,
the second RF radiator portion is in electrically conductive contact with the second RF feed within the housing,
the electrically non-conductive intermediate structure maintains a separation distance of between 0.8 and 1.5 mm between the second RF radiator portion and the base portion, and
the second RF radiator portion is electrically isolated from the base portion and the first RF radiator portion by the electrically non-conductive intermediate structure.

14. The apparatus of claim 13, wherein the second RF radiator portion has a second dimension along the transverse axis that is between 3 and 7 times longer than the longest dimension of the second RF radiator portion along the axis perpendicular to the transverse axis.

15. The apparatus of claim 14, wherein:
the second RF feed makes electrically conductive contact with the second RF radiator portion in a location that is within a first distance of the centerline, wherein the first distance is within 10% of the second dimension.

16. The apparatus of claim 15, wherein:
the location where the second RF feed makes electrically conductive contact with the second RF radiator portion is on the centerline.

17. The apparatus of claim 13, wherein:
the first RF receiver is configured to operate in one or more first frequency bands that are in the 600 MHz to 2200 MHz range, and
the second RF receiver is configured to operate in one or more second frequency bands that are in the 1.5 GHz to 2.7 GHz range.

18. The apparatus of claim 13, wherein the base portion, the first RF radiator portion, the second RF radiator portion, and the electrically non-conductive intermediate structure are a nano-molded structure, with the first RF radiator portion, the second RF radiator portion, and the base portion each having a plurality of microscopic fissures or pores and the electrically non-conductive intermediate structure having portions extending into the microscopic fissures or pores.

19. The apparatus of claim 13, further comprising a display unit, wherein:
the display unit is mounted in the housing such that a display surface of the display unit generally faces away from the wearer's skin that is placed into contact with the back surface when the wrist-wearable electronic device is worn by the wearer, and
the first RF radiator portion and the second RF radiator portions are positioned next to, and adjacent to opposing sides of, the display unit.

20. The apparatus of claim 19, wherein:
the housing is configured to be connected with a first band portion such that the first band portion is adjacent to the first RF radiator portion and with a second band portion such that the second band portion is adjacent to the second RF radiator portion,
the edges of the first RF radiator portion and the second RF radiator portion that are adjacent to the display unit have a length that is within ±5% of the length of the edges of the display unit that are adjacent to the first RF radiator portion and the second RF radiator portion, respectively, and
the edges of the first RF radiator portion and the second RF radiator portion that are furthest from the display unit have a length that is within ±5% of the length of the edges of the first band portion and the second band portion that are adjacent to the first RF radiator portion and the second RF radiator portion, respectively, when the first band portion and the second band portion are connected with the housing.

21. An apparatus comprising:
a first radio-frequency (RF) receiver having a first RF feed; and
a housing configured to be part of a wearable electronic device, wherein:
the first RF receiver and the first RF feed are located within the housing,
the housing has a plurality of exterior surfaces,
the housing includes a base portion, a first RF radiator portion, and an electrically non-conductive intermediate structure that is interposed between, and connected with, the base portion and the first RF radiator portion, the base portion includes a back surface that faces a wearer's skin that contacts the wearable electronic device when the wearable electronic device is worn by the wearer, the base portion and the first RF radiator portion are made of metal, the first RF radiator portion includes one or more of the exterior surfaces of the housing, the first RF radiator portion is positioned within the housing such that the exterior surfaces of the housing included in the first RF radiator portion generally face away from the back surface, the first RF radiator portion is in electrically conductive contact with the first RF feed within the housing, and the base portion, the first RF radiator portion, and the electrically non-conductive intermediate structure are a nano-molded structure, with the first RF radiator portion and the base portion each having a plurality of microscopic fissures or pores arising from the nano-molding manufacturing process and the electrically non-conductive intermediate structure having portions extending into the microscopic fissures or pores.

22. An apparatus comprising:
a first radio-frequency (RF) receiver having a first RF feed;
a second RF receiver have a second RF feed; and
a housing configured to be part of a wearable electronic device, wherein:
  the first RF receiver, the first RF feed, the second RF receiver, and the second RF feed are located within the housing,
  the housing has a plurality of exterior surfaces,
  the housing includes a base portion, a first RF radiator portion, and an electrically non-conductive intermediate structure that is interposed between, and connected with, the base portion and the first RF radiator portion,
  the housing further includes a second RF radiator portion,
  the electrically non-conductive intermediate structure is further interposed between, and connected with, the base portion and the second RF radiator portion,
  the base portion includes a back surface that faces a wearer's skin that contacts the wearable electronic device when the wearable electronic device is worn by the wearer,
  the base portion, the first RF radiator portion, and the second RF radiator portion are made of metal,
  the first RF radiator portion includes one or more of the exterior surfaces of the housing,
  the second RF radiator portion includes one or more further exterior surfaces of the housing,
  the first RF radiator portion is positioned within the housing such that the exterior surfaces of the housing included in the first RF radiator portion generally face away from the back surface,
  the first RF radiator portion is in electrically conductive contact with the first RF feed within the housing,
  the second RF radiator portion is positioned within the housing such that the further exterior surfaces of the housing included in the second RF radiator portion generally face away from the back surface,
  the second RF radiator portion is in electrically conductive contact with the second RF feed within the housing,
  the electrically non-conductive intermediate structure maintains a separation distance of between 0.8 and 1.5 mm between the second RF radiator portion and the base portion, and
  the second RF radiator portion is electrically isolated from the base portion and the first RF radiator portion by the electrically non-conductive intermediate structure.

23. The apparatus of claim 22, wherein:
the first RF receiver is configured to operate in one or more first frequency bands that are in the 600 MHz to 2200 MHz range, and
the second RF receiver is configured to operate in one or more second frequency bands that are in the 1.5 GHz to 2.7 GHz range.

* * * * *